(12) United States Patent
Park et al.

(10) Patent No.: US 8,313,569 B2
(45) Date of Patent: Nov. 20, 2012

(54) AIR WASHER HAVING HUMIDIFYING FUNCTION

(75) Inventors: Jun Hyung Park, Asan-Si (KR); Seung Dae Yang, Cheonan-Si (KR); Hwa Ohk Kim, Asan-Si (KR); Joon Ho Jang, Cheonan-Si (KR); Il Ho So, Asan-Si (KR)

(73) Assignee: WiniaMando Inc., Asan-si, Chungnam (KR)

( * ) Notice: Subject to any disclaimer, the term of this patent is extended or adjusted under 35 U.S.C. 154(b) by 883 days.

(21) Appl. No.: 11/942,097

(22) Filed: Nov. 19, 2007

(65) Prior Publication Data

US 2008/0127820 A1  Jun. 5, 2008

(30) Foreign Application Priority Data

| Nov. 20, 2006 | (KR) | 10-2006-0114404 |
| Dec. 29, 2006 | (KR) | 10-2006-0137433 |
| Dec. 29, 2006 | (KR) | 10-2006-0137996 |
| Dec. 29, 2006 | (KR) | 10-2006-0138604 |
| Dec. 29, 2006 | (KR) | 10-2006-0138606 |
| Dec. 29, 2006 | (KR) | 10-2006-0138608 |
| Dec. 29, 2006 | (KR) | 10-2006-0138609 |
| Dec. 29, 2006 | (KR) | 10-2006-0138610 |
| Dec. 29, 2006 | (KR) | 10-2006-0138611 |
| Dec. 29, 2006 | (KR) | 10-2006-0138612 |
| Dec. 29, 2006 | (KR) | 10-2006-0138614 |
| Mar. 2, 2007 | (KR) | 10-2007-0020905 |

(51) Int. Cl.
*B01D 53/14* (2006.01)

(52) U.S. Cl. ............. 96/282; 96/286; 96/294; 96/234; 261/83

(58) Field of Classification Search .......... 261/91, 261/92, 28, 72.1, 83–99; 96/294, 282–289; 422/1, 5, 28; 95/1, 10, 151; 55/419, 437–438
See application file for complete search history.

(56) References Cited

U.S. PATENT DOCUMENTS

| 2,922,489 | A | * | 1/1960 | Hollingsworth | 96/251 |
| 4,299,601 | A | * | 11/1981 | Schlachet | 96/282 |
| 6,832,753 | B1 | * | 12/2004 | Huang | 261/28 |
| 2005/0000911 | A1 | * | 1/2005 | Thorpe | 210/748 |

FOREIGN PATENT DOCUMENTS

| KR | 1997-0022055 | 12/1997 |
| KR | 1996-024451 | 5/1998 |
| KR | 1997-0008979 | 11/1998 |
| KR | 1997-0036283 | 2/1999 |
| KR | 2003-0032246 | 1/2004 |
| KR | 2006-0000482 | 6/2006 |
| KR | 2005-0059682 | 8/2006 |

* cited by examiner

*Primary Examiner* — Duane Smith
*Assistant Examiner* — Thomas McKenzie
(74) *Attorney, Agent, or Firm* — Lucas & Mercanti, LLP

(57) ABSTRACT

An air washer adsorbs outside contaminated air to disks, which have water films formed thereon, and settles contaminants in water in a water reservoir, thus purifying and humidifying air.

35 Claims, 27 Drawing Sheets

(a) AOS Model (16-disk)

(b) Model I (14-disk)

(c) Model II (12-disk)

(e) Model III (10-disk)

(f) Model IV (6-disk)

flow rate distribution depending on distance between disks

FIG. 29 flow rate and flow rate uniformity depending on distance between disks

| Model | | flow rate(CMM) | | flow rate uniformity | |
|---|---|---|---|---|---|
| AOS Model (16-Disk) | Front | 0.23638 | 0.5095 | 0.786012 | 0.837219 |
| | Rear | 0.27312 | | 0.888426 | |
| Model I (14-Disk) | Front | 0.3343 | 0.70305 | 0.328019 | 0.311272 |
| | Rear | 0.36875 | | 0.294524 | |
| Model II (12-Disk) | Ftront | 0.35928 | 0.78904 | 0.339596 | 0.324062 |
| | Rear | 0.42976 | | 0.308529 | |
| Model III (10-Disk) | Front | 0.46736 | 0.98661 | 0.316879 | 0.329431 |
| | Rear | 0.51925 | | 0.341984 | |
| Model VI (6-Disk) | Front | 0.6224 | 1.29651 | 0.348807 | 0.353217 |
| | Rear | 0.67411 | | 0.357627 | | flow rate and flow rate uniformity
a function go distance between disks

AIR WASHER HAVING HUMIDIFYING FUNCTION

CROSS-REFERENCE TO RELATED APPLICATIONS

This patent application claims the benefit of priority from Korean Patent Application Nos. KR10-2006-114404 filed on Nov. 20, 2006, KR10-2006-137996 filed on Dec. 29, 2006, KR10-2006-138604 filed on Dec. 29, 2006, KR10-2006-138610 filed on Dec. 29, 2006, KR10-2006-138606 filed on Dec. 29, 2006, KR10-2006-138608 filed on Dec. 29, 2006, KR10-2006-138609 filed on Dec. 29, 2006, KR10-2006-138611 filed on Dec. 29, 2006, KR10-2006-137433 filed on Dec. 29, 2006, KR10-2006-138612 filed on Dec. 29, 2006, KR10-2006-138614 filed on Dec. 29, 2006, and KR10-2007-020905 filed on Mar. 2, 2007, the contents of which are incorporated herein by reference.

BACKGROUND OF THE INVENTION

1. Field of the Invention

The present invention relates generally to air washers having humidifying functions and, more particularly, to an air washer which adsorbs outside contaminated air to disks, which have water films formed thereon, and settles contaminants in water in a water reservoir, thus purifying and humidifying air.

2. Description of the Related Art

Representative examples of conventional humidifying air washers, which purify and humidify air using a water film forming means, were proposed in Patent Document 1 and Patent Document 2. (Patent Document 1: Korean Utility Model Registration No. 20-0157935, and Patent Document 2: Korean Utility Model Registration No. 20-0292472)

A conventional air washer having a humidifying function will be described herein below with reference to Patent Document 1. Referring to FIG. 1, the reference numeral 10 denotes an upper casing, and the reference numeral 20 denotes a lower casing, which contains water therein. A motor 30 is supported in a support frame 11, which is provided in the upper casing 10. A blower fan 31 is coupled to the output shaft of the motor 30. Furthermore, a pair of rollers 40 is rotatably provided in a coupling block 12, which is provided on the lower end of the support frame 11. When power is supplied to the motor 30, the blower fan 31 is rotated, and the rollers 40 are rotated along with the blower fan 31 at the same time.

In an example, which is not shown in the drawing, a worm and a worm gear, which engage with each other, are respectively provided on the shaft of the motor 30 and shafts of the rollers 40, so that the rollers 40 are rotated by the rotation of the shaft of the motor 30. A control knob (not shown) for turning on or off the air washer and regulating the air flow rate is provided at a predetermined position on the upper casing 10.

In the drawing, the reference numeral 100 denotes a disk roller assembly. The disk roller assembly 100 includes disk rollers 101, each of which is provided by assembling disks A and disks B in a roller shape. Furthermore, the disk rollers 101, which are disposed at opposite positions, engage with the respective rollers 40 and are thus rotated in contact with the rollers 40.

In detail, the disk roller assembly 100 includes a pair of disk rollers 101, a pair of support rods, to which opposite ends of shaft rods 111 provided in the disk rollers 101 are rotatably coupled, and a handle, which is coupled to the opposite support rods.

In each disk roller 101, a plurality of the disks B are coupled to a medial portion of a support pipe, and middle support plates are coupled to opposite sides of the disks B. Furthermore, a plurality of the disks A are coupled to opposite sides of the support pipe. An end cap is coupled to each end of the support pipe.

Each of the disks A and B has a coupling hole in the center thereof. A plurality of locking notches is formed in the circumferential edge of the coupling hole. Furthermore, a plurality of cuts is formed in radial directions. A plurality of connection protrusions is provided on one surface of the disk, and connection holes are formed in the other surface of the disk at positions corresponding to the connection protrusions.

Each middle support plate has a coupling hole in the center thereof. A ring-shaped coupling rib is provided on the circumferential edge of the coupling hole. A plurality of locking notches is formed in the ring-shaped rib. A plurality of connection protrusions is provided on one surface of the middle support plate, and connection holes are formed in the other surface of the middle support plate at positions corresponding to the connection protrusions.

In the end cap, a coupling tube part is integrally provided on the central portion of the end cap body. A ring-shaped locking protrusion is provided on the end of the coupling tube part, and a plurality of circular through holes is formed around the coupling tube part. In addition, a wedge-shaped locking protrusion is provided on the outer surface of the coupling tube part.

Meanwhile, locking ribs, which are inserted into the locking notches of the disks A and B and the middle support plates, are provided on the support pipe. Furthermore, coupling stops, to which the coupling ribs of the middle support plates are fastened, are provided on the medial portion of the support pipe. A locking hole is formed in each end of the support pipe, so that, when the coupling tube part of the end cap is inserted into the end of the support pipe, the locking protrusion of the end cap is locked to the locking hole of the support pipe.

To assemble the disk roller 101, one middle support plate, for example, a right middle support plate of the two middle support plates, is positioned on the support pipe such that the locking ribs of the support pipe are inserted into the locking notches of the middle support plate. Thereafter, the middle support plate is pushed inwards on the support pipe. Then, the coupling rib of the middle support plate is fitted between the coupling stops of the support pipe, so that the middle support plate is stably fastened to the support pipe. Subsequently, the disks B are fitted over the support pipe such that the locking ribs of the support pipe are inserted into the locking notches of the disks B. Thereafter, the other middle support plate is fitted over the support pipe in the same manner as that described above, and the disks A are fitted over the support pipe at opposite sides of the middle support plates, in the same manner as the process of coupling the disks B to the support pipe. Thereafter, the shaft rod 111, which is coupled at opposite ends thereof to shaft end pipes, is inserted into the support pipe. Subsequently, each end cap is coupled to each of opposite ends of the support pipe, such that the locking protrusion provided on the coupling tube part of the end cap is the locking hole of the support pipe, and such that the ring-shape locking protrusion of the end cap is locked to the inner edge of the shaft end pipe coupled to each end of the shaft rod 111, thus completing the process of assembling the disk roller 101.

The disk rollers 101, which are assembled through the above-mentioned assembly process, are assembled into the disk roller assembly 100 by inserting the shaft end pipes of the shaft rods 111 into shaft holes, which are formed in the opposite ends of the support rod. The opposite shaft end pipes of the disk roller assembly 100 are rotatably coupled to bushings provided on the inner surface of the lower casing 20.

The disks A and B, the middle support plates, the end caps and the support pipes of the disk roller assembly 100 may be made of synthetic resin mixed with aromatic material, an antibacterial agent and a sterilizing agent, and is manufactured, for example, through injection molding processes.

In the conventional air washer having the above-mentioned construction, water is contained in the lower casing 20 to a predetermined height, and the upper casing 10 is coupled to the lower casing 20. Thereafter, when the motor 30 is operated by applied power thereto, the blower fan 31 is rotated by the rotating force of the motor 30. Simultaneously, the disk rollers 101 are rotated by the rollers 40, which are operated in conjunction with the blower fan 31. Then, water, which is smeared on the disks A and B of the disk rollers 101 to form water films, is atomized into fine particles by the centrifugal force of the disks A and B and by forced air, which is blown by the blower fan 31. The water particles and air are discharged outside the air washer through a grill type outlet port, which is formed in the sidewall of the lower casing 20, and are dispersed in the interior of a room, thus humidifying air in the room.

Here, in the case of Patent Document 1, the surface of each disk is planar, but, in the case of Patent Document 2, linear ribs (which serve to effectively draw up water and move the water towards the center of the disk) are radially provided on the surface of each disk at positions spaced apart from each other at regular intervals.

However, in the conventional arts, there are disadvantages in the structure of the disk roller assembly, so that the process of cleaning the disks is inconvenient, and contaminant settling efficiency and air humidifying efficiency of the air washer are relatively low.

SUMMARY OF THE INVENTION

Accordingly, the present invention has been made keeping in mind the above problems occurring in the prior art, and an object of the present invention is to provide an air washer having a humidifying function which has an improved structure to thus markedly enhance the contaminant settling efficiency and air humidifying efficiency.

In order to accomplish the above object, the present invention provides an air washer having a humidifying function, including: a housing having an air inlet port and an air outlet port therein; a blower fan to draw air into the housing and to discharge the air outside the housing; a disk assembly to remove foreign substances from the drawn air and to humidify the drawn air; and a drive unit to operate the blower fan and the disk assembly, wherein the disk assembly comprises a disk shaft and a disk fitted over the disk shaft.

The present invention, having the above-mentioned construction, is advantageous in that the contaminant settling efficiency and air humidifying efficiency thereof can be enhanced.

In the air washer of the present invention, a disk assembly includes a disk shaft, which has a stop ring on a first end thereof, disks, which are fitted over the disk shaft, and an end cap, which is coupled to one end of the disk shaft. Therefore, when assembling the disk assembly, because the disks are fitted over the disk shaft in one direction and the end cap is coupled to the disk shaft in the same direction, there is an advantage in that the assembly process is simplified, so that the working hours for the assembly process is reduced.

The disks are divided into a plurality of disk sets. A spacer is fitted over a disk shaft between the disk sets. Gear teeth are formed on the circumferential outer surface of the spacer. Thus, the spacer serves both to maintain the distance between the disk sets constant and to transmit rotating force from a motor to the disk shaft.

Furthermore, a flange is provided on the end cap, and a mounting protrusion is provided on the end of the disk shaft. The mounting protrusion is bent in the circumferential direction of the disk shaft. An insert slot, into which the mounting protrusion is inserted, is formed in the flange. Thus, there is an advantage in that the process of assembling the end cap to the disk shaft is simple.

Each disk has a planar shape, and a plurality of ribs is provided on the surface of the disk in approximately radial directions. A stopper protrudes from the inner end of each rib. Therefore, a large amount of water can remain on the disk for a long time.

Furthermore, a curved part, which is convex in the direction opposite the direction in which the disk is rotated, is formed in each rib. A bent part, which is bent to be convex in the direction opposite the direction in which the disk is rotated, is formed in each rib between the curved part and the stopper. Thus, when the disks are rotated, a large amount of water can be drawn up by the curved parts. As well, thanks to the bent parts, water is prevented from being removed from the disks even when the disks are rotated.

The air washer of the present invention further includes a switch. The switch includes a switch body, and a switching bar, which is provided on the switch body to turn on or off the power of the air washer. A support member for supporting the switching bar is provided in the lower housing, so that, when the upper housing is separated from the lower housing, the supply of power to the air washer is automatically interrupted. Therefore, when a user separates the upper housing from the lower housing to supplement water or clean the disks, the user can be prevented from being injured by a blower fan or other components, and the air washer is prevented from being damaged.

The air washer further includes a bracket, which is provided in the upper housing and has therein a switch seat, into which the switch is seated. Two first mounting hooks are provided at opposite positions in the bracket, and two second mounting hooks are provided in the upper housing at positions corresponding to the respective first mounting hooks. Thus, the switch can be easily installed in the housing through a simple installation structure.

Furthermore, the bracket further includes locking hooks, which are provided in the bracket at opposite sides of the switch seat. Thus, the switch can be securely mounted to the bracket using the locking hooks.

In addition, a handle seat, into which a grip part of a disk shaft handle is seated, is formed in the housing, so that the disk shaft handle can be stably placed in the housing. Thus, the disk shaft handle is prevented from being undesirably moved to the left or right, thereby reducing noise attributable to friction.

As well, a surface of the part of the housing, which has the handle seat defined therein, is inclined at a predetermined angle, so that the disk shaft handle, which is placed in the housing in a state in which it is fitted over the disk shaft, can maintain its position more stably.

A support rib is vertically provided on the inner surface of the housing, and the handle seat is formed in the upper edge of the support rib. Therefore, the space for forming the handle seat is relatively small, so that the space inside the housing is increased.

In addition, the disk shaft has a cross-section such that the upper and lower portions thereof are asymmetrical to each other, based on the horizontal line passing through the center thereof, and such that the left and right portions thereof are asymmetrical to each other based on the vertical line, passing through the center thereof. Therefore, the disks are prevented from being fitted over the disk shaft in the wrong direction.

Moreover, the disk shaft is shaped such that a cross-section thereof has a symmetrical structure with respect to the diagonal direction based on the center thereof. Thus, when the disks are placed on the support surface in a state in which they are fitted over the disk shaft, the disks remain balanced and thus maintain the stationary state.

Furthermore, the opposite ends of the disk shaft, over which the disks are fitted, are differently shaped from each other, so that the disks are prevented from being rotated in the wrong direction, thus power can be reliably transmitted from the drive unit to the disk shaft. Particularly, in the case where the arc-shaped ribs are formed on the surface of the disks, the disk shaft can be installed in the correct direction, in which the ribs can correctly draw up water, thus improving the contaminant settling efficiency and air humidifying efficiency of the air washer.

Meanwhile, shaft seats are formed in the supports for supporting the disk shaft. The disk shaft has a support protrusion on the second end thereof, such that the second end of the disk shaft, having the support protrusion, is longer than the first end thereof. Furthermore, a stop piece is provided in one of the shaft seats, which are shaped differently from each other. Therefore, even if an attempt is made to seat the second end of the disk shaft into the shaft seat having the stop piece, because the support protrusion interferes with the stop piece, incorrect assembly can be fundamentally prevented.

In the present invention, air inlet ports have inlet air guide blades. Thus, efficiency with which air flows towards the center of the blower fan can be increased, thus enhancing the contaminant settling efficiency and air humidifying efficiency of the air washer.

Furthermore, when seen in a plan view, each of the four sidewalls of the housing has a concave arc shape. The air inlet ports are formed in three regions in the upper surface of the housing, that is, in the rear portion and opposite side portions of the upper surface of the housing. In addition, the inlet air guide blades are inclined downwards towards the center of the blower fan and are arranged in an arc-shaped arrangement along the sidewalls of the housing. Therefore, the external appearance of the air washer is superior, and the efficiency with which air is drawn towards the center of the blower fan is improved, thus further enhancing the contaminant settling efficiency and air humidifying efficiency of the air washer.

In the present invention, a sterilizing unit is provided in the water reservoir. Therefore, the present invention does not require a process of mixing liquid sterilizing agent with water in the water reservoir, thus being convenient for the user.

Furthermore, the sterilizing unit is disposed ahead of front sides of the disks, which are parts of the disks that enter water when the disks are rotated. As such, because the sterilizing unit is disposed at a position at which water currents are generated, sterilizing substances can be smoothly drawn out of the sterilizing unit, and the sterilizing substances can be evenly dispersed in water in the water reservoir.

In addition, in the case where the disks are divided into a first disk set and a second disk set, the sterilizing unit is disposed between the first and second disk sets, ahead of front sides of the disks, thus further enhancing the efficiency with which the sterilizing substances are eluted from the sterilizing unit and are dispersed in water in the water reservoir.

Meanwhile, installation protrusions for supporting the receiving frame of the sterilizing unit are provided in the housing. A cut slot is formed in each installation protrusion in the direction in which the receiving frame is fitted into the installation protrusions. Thus, when the receiving frame is fitted into or removed from the installation protrusions, the installation protrusions can be elastically moved, so that the process of assembling or removing the receiving frame can be smoothly conducted.

Meanwhile, to determine the optimum distance between disks in the disk assembly, the present invention uses a method in which, after several models, which have various flow rates and flow rate uniformities depending on the distances between disks, are sampled, the model that has the largest number of disks despite having a low flow rate uniformity is determined to be the optimum model. Thus, the humidifying efficiency, accomplished by the rotation of the disks, can be enhanced.

Alternatively, in the method of determining the optimum distance between disks in the disk assembly, a method in which several models, which have various flow rates and flow rate uniformities depending on the distances between disks, are sampled, and, thereafter, among the sampled models, a model, the flow rate uniformity of which is 0.35 or less, is determined to be the optimum model, may be used. Thus, the humidifying efficiency attributable to the rotation of the disks can be further enhanced.

Moreover, the present invention may be constructed such that the distance between the disks of the disk assembly ranges from 6.5 mm to 6.8 mm to maximize the humidifying efficiency accomplished by the rotation of the disks.

Meanwhile, in the present invention, a support holding part may be provided on the bottom of the water reservoir, such that the disk shaft of the disk assembly can be temporarily fastened to the support holding part. In this case, when it is desired to clean the disks, the disk assembly is removed from the housing, and, thereafter, the disk shaft of the disk assembly is temporarily fastened to the support holding part. Subsequently, the disk assembly is disassembled, and the operation of cleaning the disks is conducted. Therefore, the cleaning operation can be conveniently conducted. Furthermore, compared to the conventional art, in which the disk assembly is separated from the water reservoir and is moved outside the water reservoir to conduct the cleaning operation, the present invention can solve a problem in which water falls onto the support surface when the disk assembly is moved outside the water reservoir. In addition, the present invention prevents the disks from being damaged, which may occur when they are moved. As well, the present invention can solve a problem in that, when the disk assembly is disassembled and various elements of the disk assembly are thus placed on the support surface, a relatively large amount of space is required.

Furthermore, a support means, which can support the disks when the disk shaft is fastened to the support holding part, is provided in the water reservoir. Therefore, when the disk assembly is fastened to the support holding part to conduct the operation of cleaning the disks, the outer edges of the disks can be stably supported by the support means. Thus, during the process of assembling or disassembling the disk assembly, the disk assembly is reliably prevented from being undesirably moved forwards, backwards, leftwards or rightwards.

Here, the supports for supporting the disk shaft or handle parts, which are formed by protruding the bottom of the water reservoir inwards, are used as the support means. Therefore, the structure of the support means for supporting the disks is simple.

Furthermore, in the case where the handle parts and support frames, which are provided on the handle parts to support the disks, are used as the support means, there is an advantage in that the utilization of space in the water reservoir can be increased.

Meanwhile, a rolling prevention means may be formed on the circumferential outer edge of each disk. In this case, even if the disk assembly is placed on the support surface, for example, to conduct the operation of cleaning the disks, the disk assembly is prevented from undesirably rolling on the support surface.

In the case where the rolling prevention means is realized by cutting parts of the outer edges of the disks, there are advantages in that the process of manufacturing the disk is simple and the weight of the disk is reduced.

Furthermore, in the present invention, an outer rim is provided on the surface of each disk at a position spaced apart from the fitting hole of the disk. Thus, the distance between adjacent disks can be maintained constant using the outer rim. In addition, the outer rim serves to prevent water from entering the fitting hole of the disk, so that, even when the disks are used for a long time, foreign substances are prevented from being held in the fitting hole.

Moreover, an inner rim is provided between the fitting hole and the outer rim. Therefore, the inner rim and the outer rim form a double water permeation structure, such that water is prevented from entering the fitting hole of the disk.

Meanwhile, in the present invention, a shroud, which surrounds the blower fan, is provided in the housing such that it protrudes from the housing, thus reducing noise attributable to the operation of the blower fan, and increasing the flow rate of air drawn into the housing by the blower fan.

Furthermore, an air inflow passage, which is defined in the first upper housing, has a rectangular cross-section, and an air inflow passage, which is defined by the shroud, has a circular cross-section. Therefore, when air is drawn into the housing by the blower fan, air currents are rapidly varied, and the generation of an air vortex is promoted, thus reducing noise and increasing the flow rate of air.

BRIEF DESCRIPTION OF THE DRAWINGS

The above and other objects, features and advantages of the present invention will be more clearly understood from the following detailed description taken in conjunction with the accompanying drawings, in which:

FIG. 29 is a table showing results of tests for flow rates and flow rate uniformities according to a distance between the disks.

DESCRIPTION OF THE PREFERRED EMBODIMENTS

Hereinafter, a preferred embodiment of the present invention will be described in detail with reference to the attached drawings.

Figure 1:
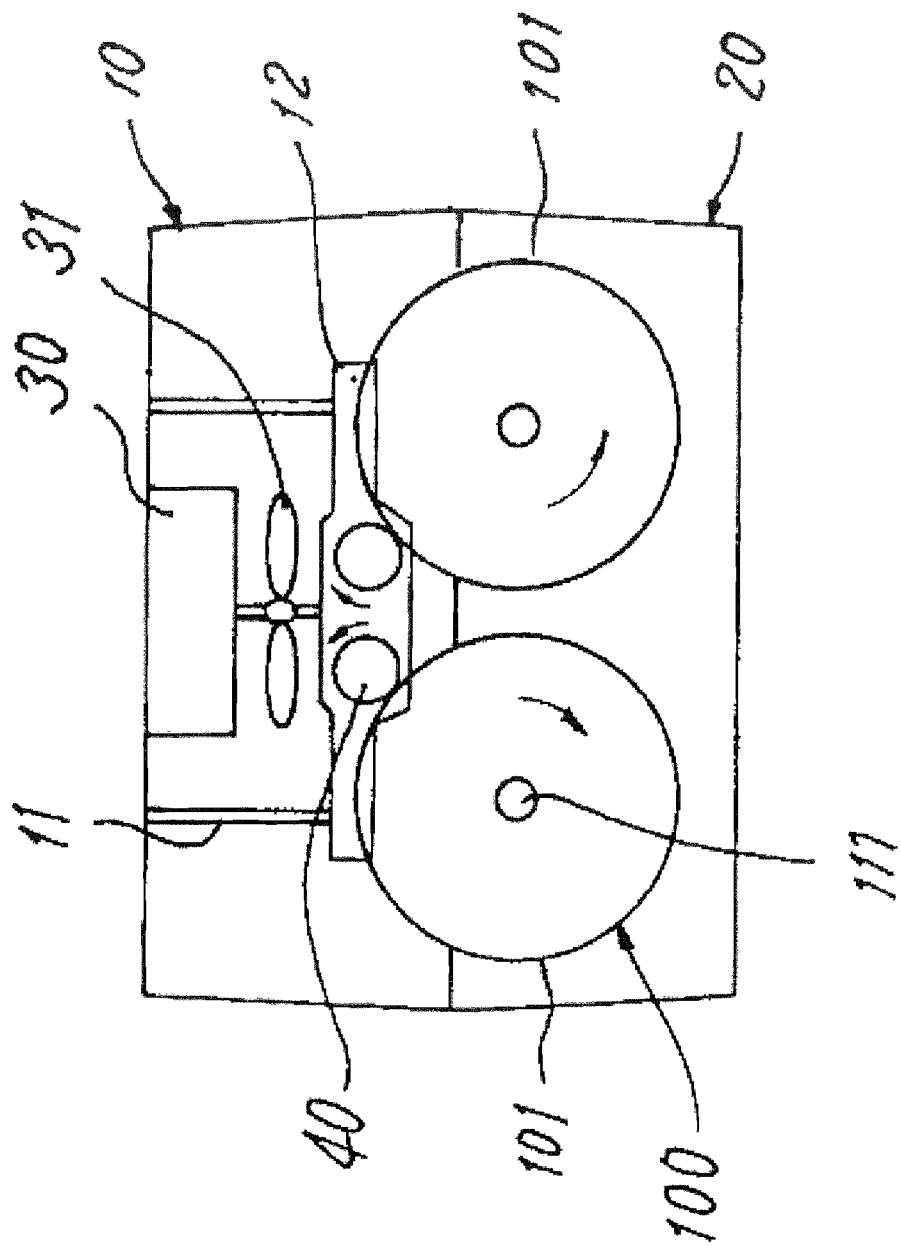
FIG. 1 is a schematic view showing a conventional air washer having a humidifying function.
Figure 2:
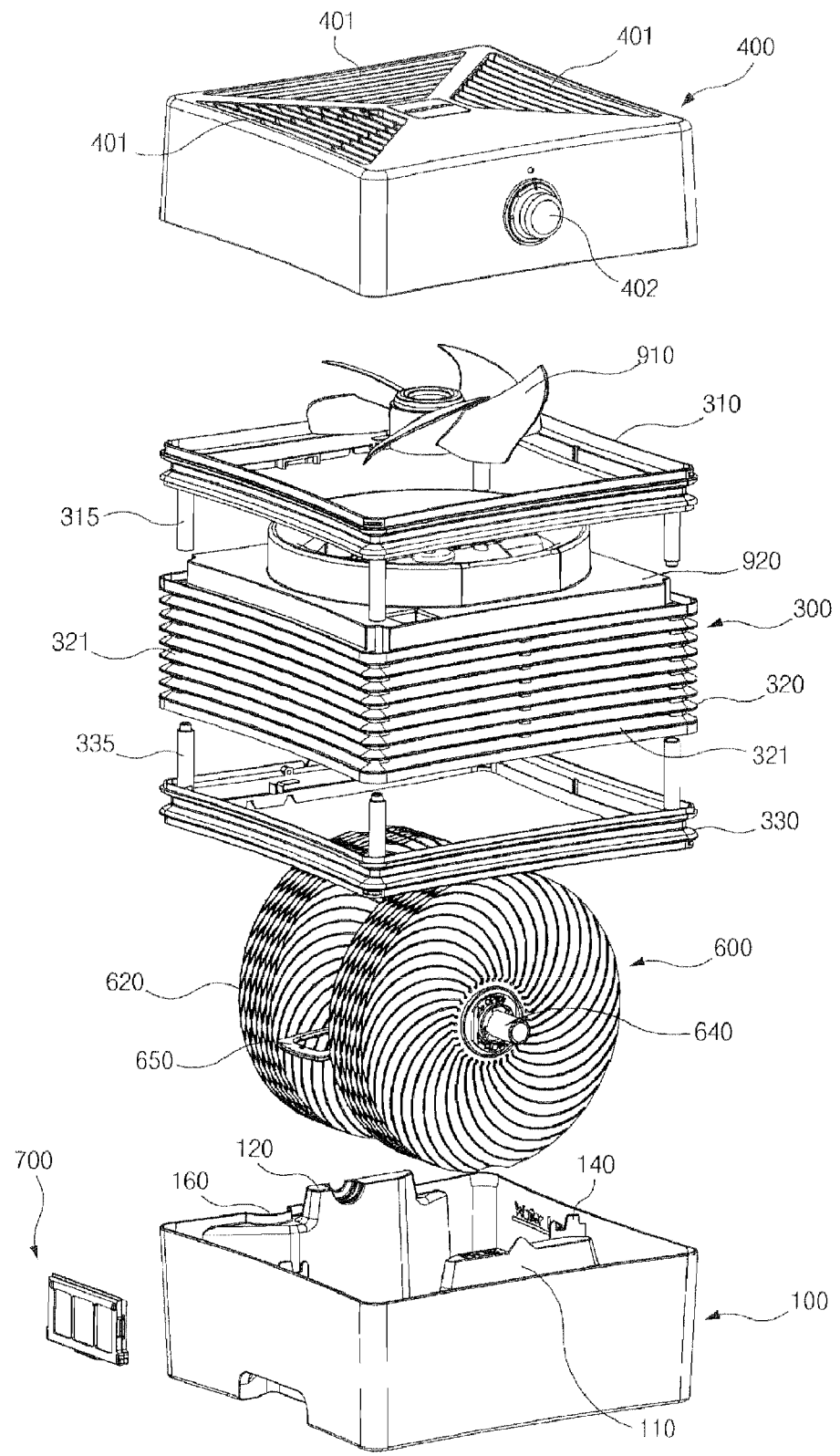
FIG. 2 is an exploded perspective view of an air washer having a humidifying function, according to a preferred embodiment of the present invention.
Figure 19:
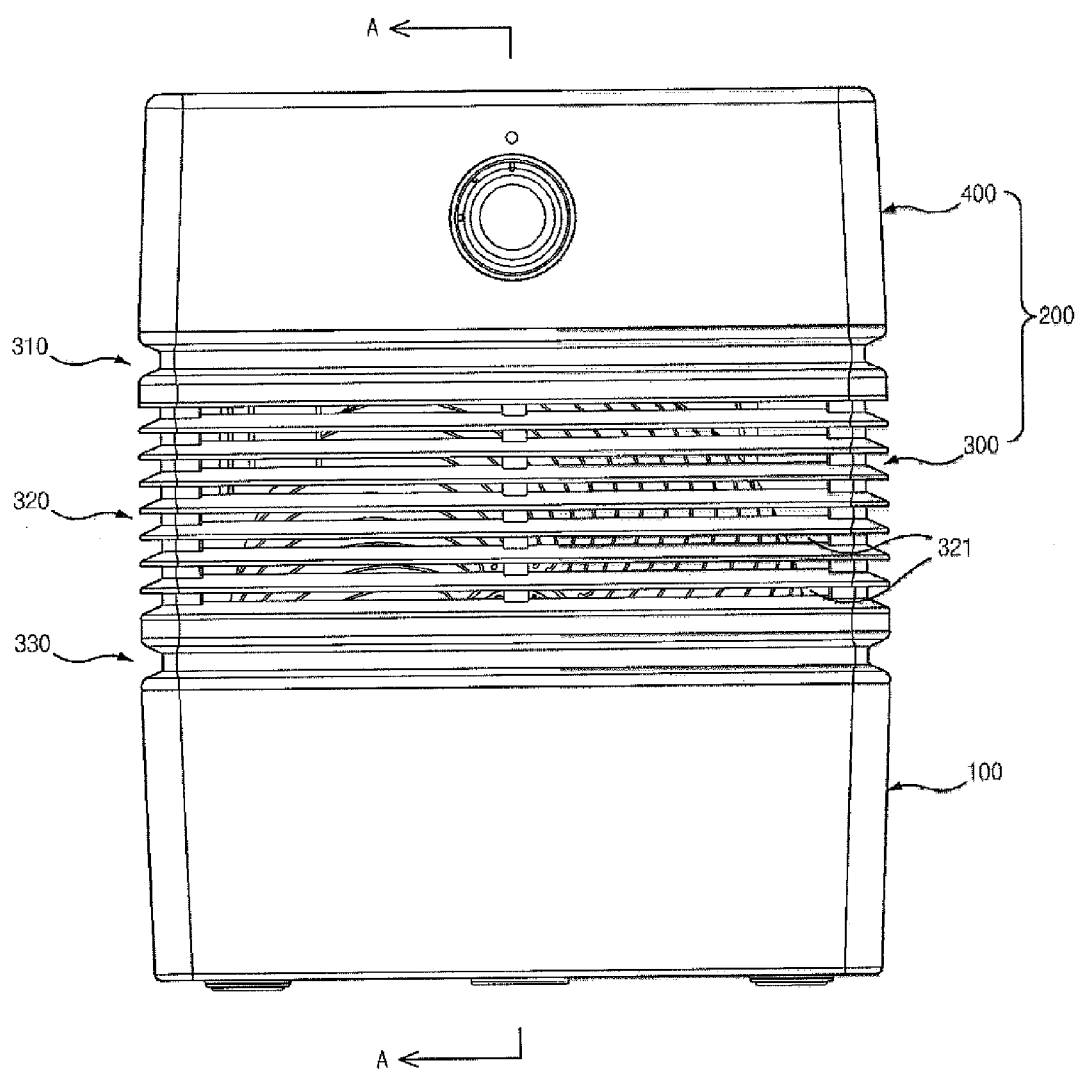
FIG. 19 is a front view showing the assembled air washer of FIG. 2.
Figure 20:
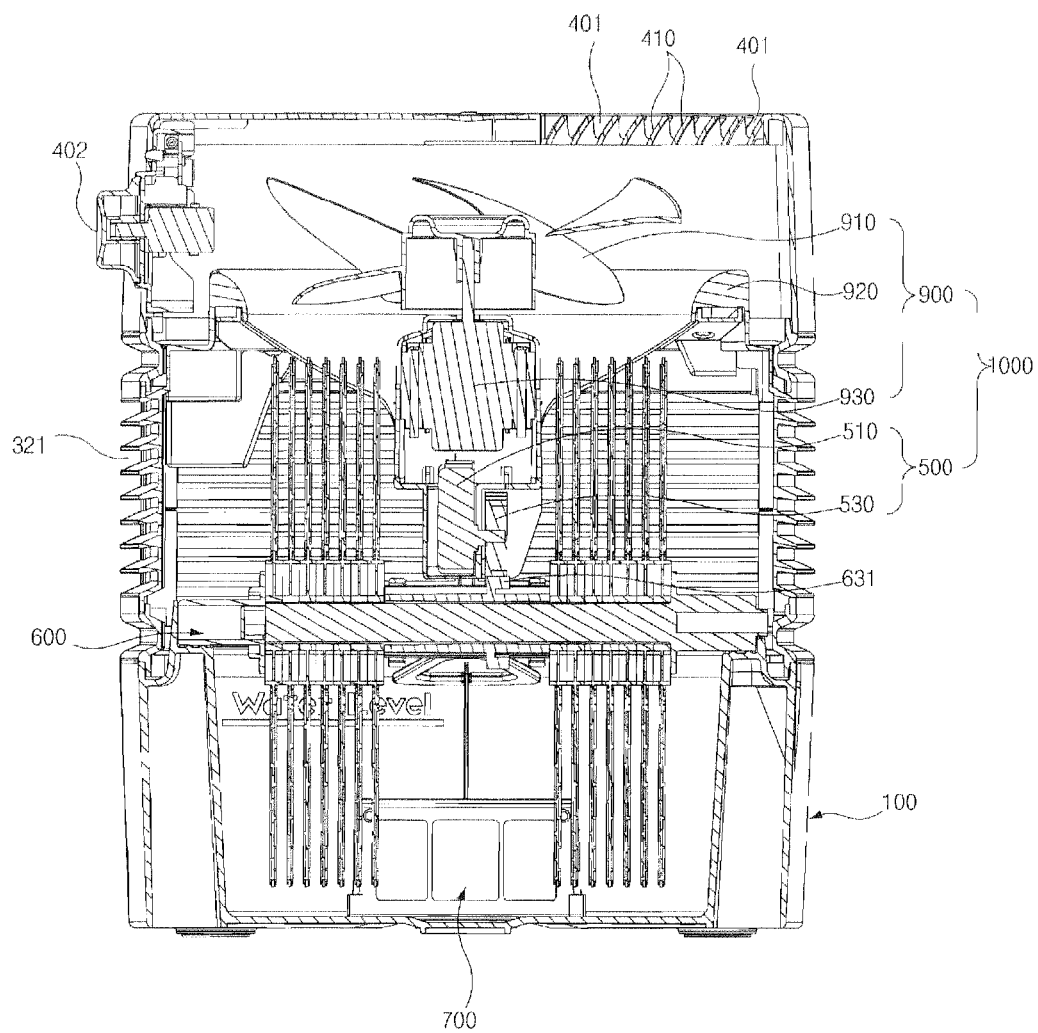
FIG. 20 is a sectional view taken along the line A-A of FIG. 19.
Figure 21:
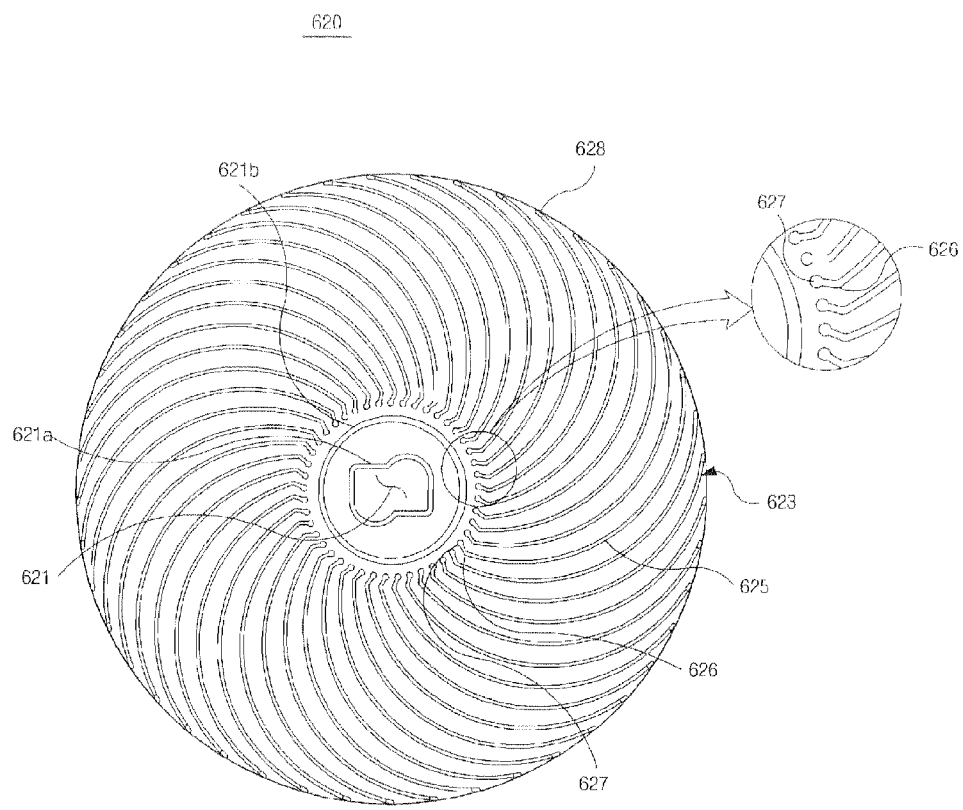
FIG. 21 is a front view of an air cleaning disk of the air washer according to the present invention.

FIG. 2 is an exploded perspective view of an air washer having a humidifying function, according to a preferred embodiment of the present invention. FIG. 19 is an assembled front view of FIG. 2. FIG. 20 is a sectional view taken along the line A-A of FIG. 19.

As shown in FIGS. 2 through 4, 19 and 20, the air washer according to the embodiment of the present invention comprises a housing, a main air washer body, which is provided in the housing, and a switch 800, which is provided in an upper housing 200 of the housing. The switch 800 includes a switch body, and a switching bar 830, which is provided on the switch body to turn on or off the power of the air washer. A support member for supporting the switching bar 830 is provided in a lower housing 100 of the housing.

The housing includes the upper housing 200 and the lower housing 100, which is coupled to the lower end of the upper housing 200. The lower housing 100 comprises a water reservoir 100 for containing water. The upper housing 200 includes a first upper housing 400 and a second upper housing 300, which is disposed between the first upper housing 400 and the lower housing 100.

The first upper housing 400 has a box shape which has a rectangular upper surface and sidewalls provided around the upper surface. A plurality of air inlet ports 401 is formed through the upper surface of the first upper housing 400.

The air inlet ports 401 may be formed in the entire area of the upper surface of the first upper housing 400 such that a cross-section of an air inflow path has a rectangular shape.

Figure 4:
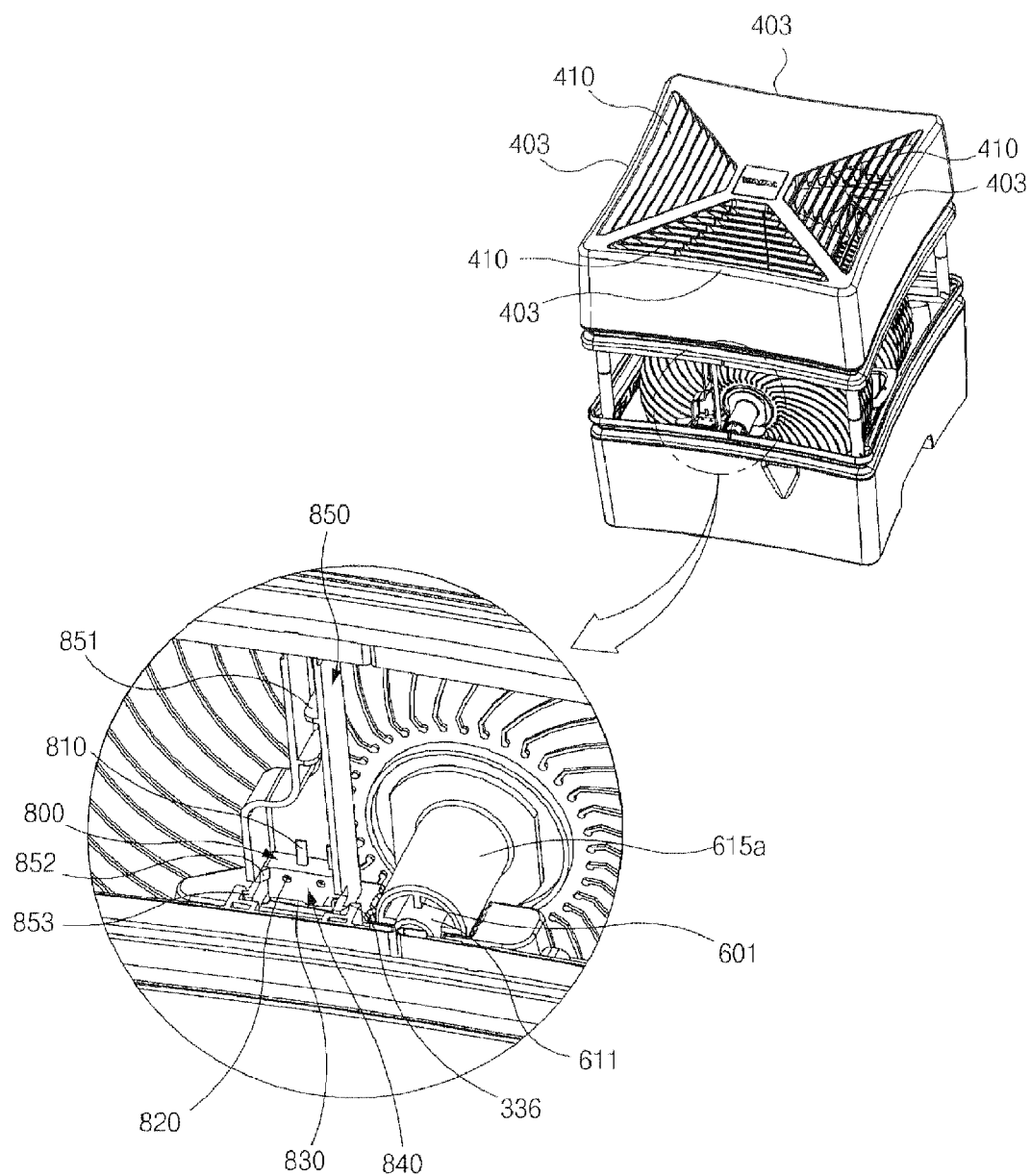
FIG. 4 is a perspective view showing the installation of a switch of the air washer according to the present invention.

As shown in FIG. 4, when seen in a plan view, each of the four sidewalls 403 of the first upper housing 400 has a concave arc shape.

Preferably, each air inlet port 401 has a grill shape. In this embodiment, the air inlet ports 401 are formed in three regions in the upper surface of the first upper housing 400, other than the front region of the upper surface thereof. In other words, no air inlet port is preferably formed above a position at which a control knob 402, which will be explained later herein, is disposed. Furthermore, it is preferable that each of the air inlet ports 401, formed in the upper surface of the first upper housing 400, has a triangular shape, in which the air inlet port 401 is reduced in width from the outside to the center.

Particularly, as shown in FIGS. 4 and 20, inlet air guide blades 410 are provided in each air inlet port 401. Each inlet air guide blade 410 is inclined at a predetermined angle such that inlet air flows towards the center of a blower fan 910, thus increasing the efficiency with which air flows towards the center of the blower fan 910. Furthermore, because inlet air flows towards the center of the blower fan 910, noise, attributable to movement of air around the blower fan 910, in particular, between the first upper housing 400 and a casing 920, can be markedly reduced.

In addition, as shown in FIG. 4, each inlet air guide blade 410 is bent to have an arc shape such that the medial portion thereof is adjacent to the center of the blower fan 910 (that is, the inlet air guide blade has a shape and inclination corresponding to those of the corresponding arc-shaped sidewall of the upper surface of the first upper housing), thus increasing the flow rate of air towards the center of the blower fan 910, thereby enhancing contaminant settling efficiency and air humidifying efficiency.

Meanwhile, a dial type control knob 402 is provided on the front sidewall of the first upper housing 400, so that the settling volume and the humidifying rate of the air washer can be controlled by adjusting the speeds at which a blower 900 and a disk assembly 600 are rotated using the control knob 402.

The second upper housing 300 includes a first frame 310, an intermediate body 320, which is provided under the first frame 310, and a second frame 330, which is provided under the intermediate body 320.

The first frame 310 and the second frame 330 have rectangular ring shapes corresponding to the cross-sections of the first upper housing 400 and the lower housing 100, respectively. Furthermore, a first coupling rod 315 having a cylindrical shape protrudes downwards from each corner of the first frame 310.

In the same manner, a second coupling rod 335 protrudes upwards from each corner of the second frame 330. A reduced-diameter part having a reduced cross-sectional area is provided on an end of each second coupling rod 335. An internal thread is formed on the inner surface of the reduced-diameter part such that a locking bolt can be screwed into the reduced-diameter part. In addition, a seating step, onto which the head of the locking bolt is seated, is formed in the second coupling rod 335 by the reduced-diameter part. The reduced-diameter parts of the second coupling rods 335 are inserted into the respective first coupling rods 315 of the first frame 310.

As well, an internal thread for engagement with the locking bolt is formed on the inner surface of the end of each first coupling rod 315.

In contrast to the above description, a reduced-diameter part may be provided on each first coupling rod 315 of the first frame 310.

Figure 3:
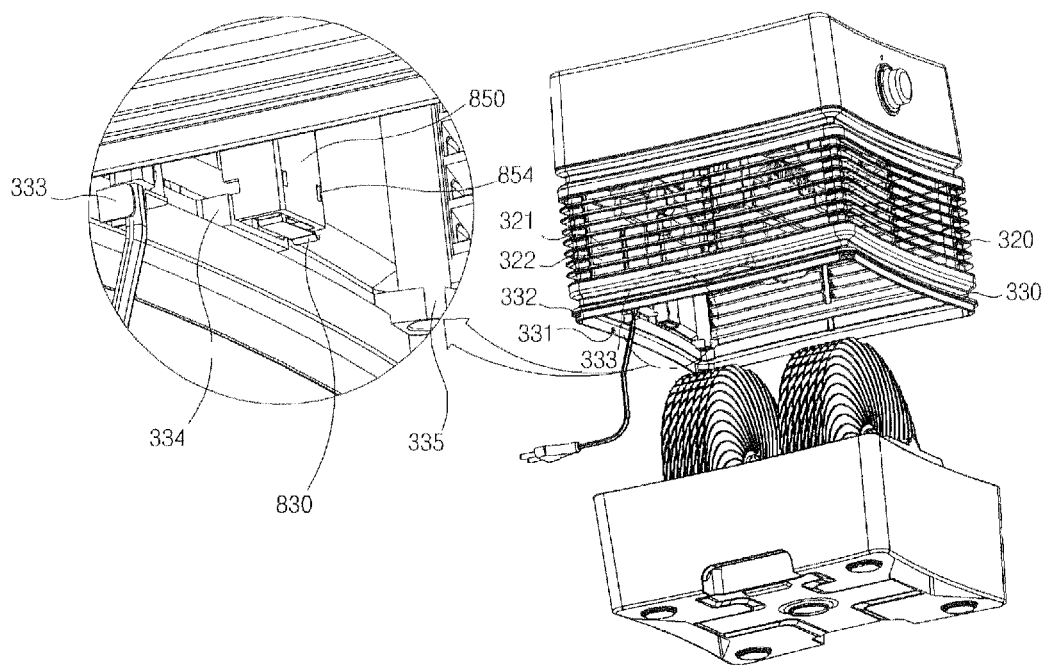
FIG. 3 is a partial perspective view showing the internal construction of an upper housing of the air washer of FIG. 2.

Furthermore, as shown in FIG. 3, support ribs for coupling the second coupling rods 335 to the second frames 330 may be provided in the second frame 330 to increase the strength thereof. In addition, a through hole 332 is formed in each corner of the first and second frames 310 and 330.

Meanwhile, locking protrusions are provided at upper and lower positions on the outer surface of each of the first and second frames 310 and 330. The upper locking protrusion of the first frame 310 is locked to the first upper housing 400, and the lower locking protrusion thereof is locked to the upper end of the intermediate body 320.

Furthermore, the upper locking protrusion of the second frame 310 is locked to the lower end of the intermediate body 320, and the lower locking protrusion thereof is locked to the lower housing 100.

In addition, two V-shaped lead notches 331 for guiding wires are formed in the lower edge of the second frame 330.

A wire guide 333 is provided on the inner surface of the second frame 330 above the space between the two lead notches 331. The wire guide 333 includes a first guide piece and a second guide piece, which are spaced apart from each other by a predetermined distance. The wires are inserted between and guided by the first and second guide pieces. The second guide piece is bent to have an 'L' shape.

Furthermore, an insert hole, into which a locking bolt is inserted, is formed in the inner surface of the second frame 330, above the second guide piece. A wire bracket, which supports the wires therein, is fastened to the second frame 330 on the second guide piece by the locking bolt, which is tightened into the insert hole through the wire bracket. Thereby, the wires can be maintained at the correct position. As such, the second guide piece serves to support the wire bracket, as well as guiding the wires.

In the second frame 330, a switch mounting part 334 is formed on the inner surface of the sidewall, on which the wire guide 333 is provided.

Figure 6:
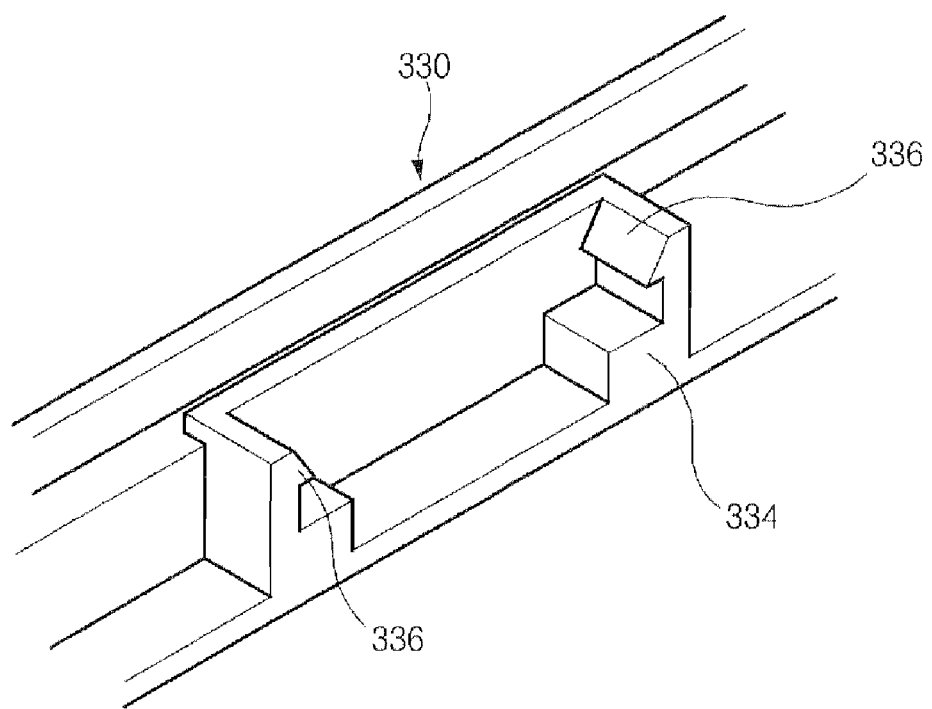
FIG. 6 is a partial perspective view showing a second frame of the air washer according to the present invention.

As shown in FIGS. 4 and 6, the switch mounting part 334, which is formed in the second frame 330 of the upper housing, has a depression shape and includes two second mounting hooks 336, each of which protrudes to a predetermined length. Each second mounting hook 336 has an inclined inner surface such that the thickness thereof is reduced from the outer end thereof to the inner end, that is, towards the center of the switch mounting part 334. Furthermore, the two second mounting hooks 336 are oriented such that the inclined surfaces thereof face each other.

In addition, protrusions are provided in the switch mounting part 334 below the respective second mounting hooks 336. The protrusions are spaced apart from each other by a predetermined distance. Each protrusion is spaced apart from the corresponding second mounting hook 336. That is, a space is defined between each protrusion and the corresponding second mounting hook 336. A groove is formed in each protrusion in the vertical direction of the air washer.

The intermediate body 320 has a pipe shape, which has a rectangular cross-section and is open at upper and lower ends thereof. Air outlet ports 321, each of which has a grill shape, are formed through the front surface and the opposite side surfaces of the intermediate body 320. Support frames, which are provided in each air outlet port 321, are arranged in a horizontal direction and are inclined at predetermined angles.

The rear surface of the intermediate body 320 forms a mounting wall 322. A bracket seat, which is formed by opposite protrusions such that the bracket 850 is fitted thereinto, is provided on the inner surface of the mounting wall 322.

Furthermore, a coupling hole, corresponding to the surface shape of the corresponding coupling rods 335, is longitudinally formed in each corner of the intermediate body 320. The casing 920 is horizontally provided in the upper end of the intermediate body 320. A through hole, through which air passes, is formed through the central portion of the casing 920. In addition, a hole, through which the corresponding coupling rod is inserted, is formed in each corner of the casing 920. A wire lead hole, through which the wires, connected to the control knob 402, are inserted, is vertically formed in the casing 920.

Figure 24:
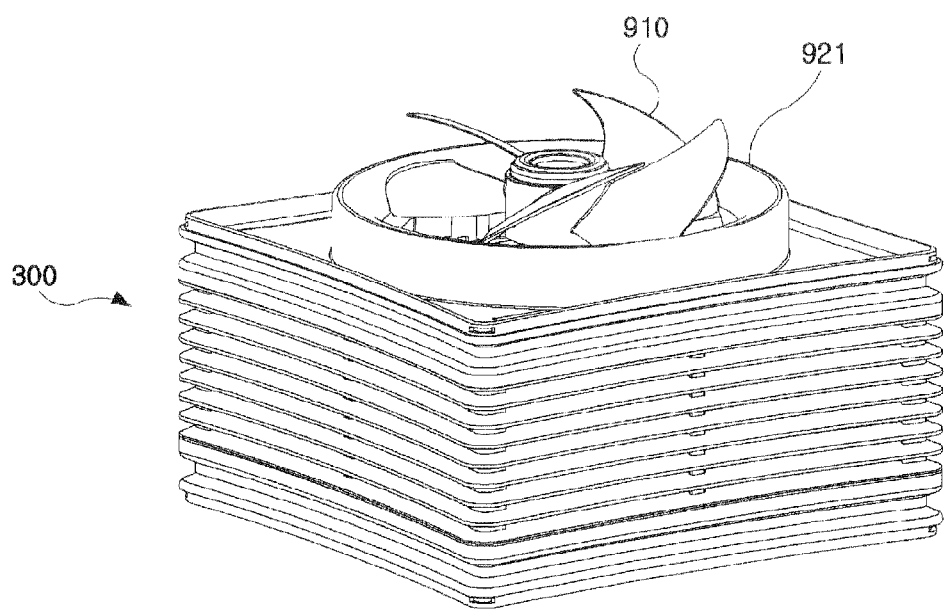
FIG. 24 is a perspective view showing the construction surrounding a blower fan according to the present invention.

Meanwhile, FIG. 24 illustrates the construction around the blower fan 910.

As shown in FIG. 24, a circular shroud 921 is provided on the casing 920, which is the upper surface of the second upper housing 300, and in which the blower fan 910 is installed. In detail, the shroud 921 is provided along the edge of the through hole, which is formed in the casing 920 around the blower fan 910, so that the shroud 921 has a shape such that it surrounds the blower fan 910.

As such, because the shroud 921 has a circular shape, the air inflow path also has a circular cross-section. Furthermore, the shroud 921 has a smoothly curved inner surface, so that air drawn into the air washer can be smoothly guided along the inner surface of the shroud 921.

Here, the shroud 921 has a structure such that it protrudes upwards from the casing 920, which has the through hole and is provided in the upper end of the second upper housing 300.

To assemble the upper housing 200, having the above-mentioned construction, the first frame 310 is fastened to the first upper housing 400. Thereafter, the first coupling rods 315 of the first frame 310 are inserted into the corresponding coupling holes, which are formed in the respective corners of the intermediate body 320. Subsequently, the second coupling rods 335 of the second frame 330 are inserted into the corresponding coupling holes of the intermediate body 320, and, simultaneously, the ends of the second coupling rods 335 are fitted into the corresponding first coupling rods 315. Thereafter, the locking bolts are inserted into the respective second coupling rods 335 and are tightened into the respective first coupling rods 315, thus completing the assembly of the upper housing 200.

Of course, those skilled in the art will appreciate that the first frame 310, the intermediate body 320 and the second frame 330 may be integrated with each other into a single body to form the second upper housing having a single body. In this case, the second upper housing, having a single body, may be called a discharge frame 300.

The main air washer body is disposed in the housing and serves to draw indoor air, to settle foreign substances, contained in the air, in water such that foreign substances are removed from the air, and to discharge fresh air after humidifying the fresh air, in the same manner as in the conventional art.

Figure 5:
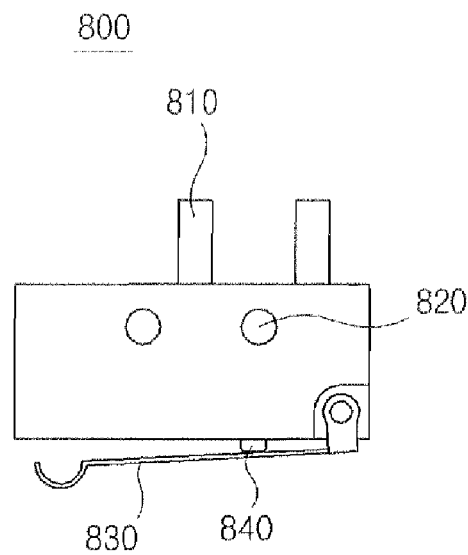
FIG. 5 is a side view of the switch of FIG. 4.

As shown in FIGS. 4 and 5, the switch 800 is installed in the upper housing and includes the switch body, and the switching bar 830, which is provided on the switch body to turn on or off the power of the air washer.

In detail, two connection terminals 810 protrude from the upper end of the switch body. A micro switch may be used as the switch body.

One of the connection terminals 810 is connected to a power supply wire, and the remaining one thereof is connected to a drive unit 1000. Furthermore, a tact switch 840 is provided in the lower end of the switch body. In addition, insert holes 820 are formed at both sides of the switch body.

The switching bar 830 is disposed below the tact switch 840 of the switch body and is rotatably coupled at a first end thereof to the switch body. In this embodiment, a plate spring is used as the switching bar 830, so that, when external force is applied thereto, the switching bar 830 is elastically bent and thus pushes the tact switch 840, and, when the force is removed, it is separated from the tact switch 840.

Therefore, the switching bar 830 serves to connect or disconnect the drive unit 1000 to or from the power supply wire to allow or interrupt the supply of power to the air washer.

In this embodiment, a downwards curved part is formed on an end of the switching bar 830 having the planar shape.

The construction of this switch 800 is the same as that proposed in Korean Utility Model Laid-Open Publication 1998-0032017, and therefore, for further explanation, reference is to be made to this publication.

When the upper housing 200 having the switch 800 is assembled with the lower housing 100, the switching bar 830 is brought into contact with a second support 120, which is provided in the lower housing 100. Thereby, the switching bar 830 is rotated, thus pushing the tact switch 840. As a result, the drive unit 1000 is connected to the power supply wire.

In contrast, when the upper housing 200 is separated from the lower housing 100, the switching bar 830 is removed from the second support 120 of the lower housing 100, so that the switching bar 830 is returned to its original position, thus releasing the tact switch 840. Therefore, the drive unit 1000 is disconnected from the power supply wire.

As such, the present invention is constructed such that, when the upper housing 200 is separated from the lower housing 100, the supply of power to the air washer is automatically interrupted. Therefore, when a user separates the upper housing 200 from the lower housing 100 to add water or clean the disks 620, the user can be prevented from being injured by the blower 900 or other components.

The bracket 850 is provided on the inner surface of the rear wall of the intermediate body 320 of the upper housing and provides a switch seat, into which the switch 800 is seated. The switch seat extends a predetermined length in the vertical direction of the air washer. The bracket 850 includes a switch installation part, in which the switch 800 is installed, and a guide part, which is formed above the switch installation part.

The switch installation part has a size corresponding to the size of the switch 800. The guide part has a cross-sectional area less than that of the switch installation part. First mounting hooks 853 are provided at opposite positions on the lower end of the switch installation part such that they face and are aligned with the corresponding second mounting hooks 336. That is, each first mounting hook 853 has an inclined inner surface such that the thickness thereof is increased towards the center of the air washer.

Furthermore, locking hooks 852 are provided in the switch installation part of the bracket 850 on opposite sides of the switch seat. The locking hooks 852 are disposed above the first mounting hook 853. The locking hooks 852 are formed by cutting and bending parts of the opposite sidewalls of the bracket 850. Each locking hook 852 has an inclined inner surface such that the thickness thereof is reduced from the outer end thereof to the inner end.

In addition, insert protrusions 854, which are inserted into the respective insert holes 820 of the switch 800, are provided on the inner wall of the bracket 850 between the opposite locking hooks 852. Each insert protrusion 854 is formed by compressing part of the outer surface of the inner wall of the bracket 850 inwards.

To assemble the switch 800 with the bracket 850 having the above-mentioned construction, when the switch 800 is inserted into the switch seat of the bracket 850, the switch 800 is moved inwards along the inclined surfaces of the locking hooks 852, and is locked by the locking hooks 852. Simultaneously, the insert protrusions 854 of the bracket 850 are inserted into the respective insert holes 820 of the switch 800, thus completing the assembly process. As such, in the present invention, the switch 800 can be securely fastened to the bracket 850.

The bracket 850, which is assembled with the switch 800, is inserted between the second mounting hooks 336 such that the first mounting hooks 853 of the bracket 850 are locked to the second mounting hooks 336. Thereby, the switch 800 is installed in the intermediate body 320 of the upper housing 200.

As such, the switch 300 can be assembled with the bracket 850 in a one-touch assembly manner, and the bracket 850 can also be assembled with the upper housing 200 in a one-touch assembly manner. Thanks to this simple structure, there is an advantage of ease of the assembly process.

Furthermore, there is an advantage in that the switch 300 is reliably and securely installed in the upper housing 200 using the bracket 850.

A plurality of guide protrusions 851 is provided in the inner surfaces of the opposite sidewalls of the guide part of the bracket 850. The guide protrusions 851 are disposed on the opposite sidewalls of the guide part at positions at which they are misaligned with each other.

Thus, electric connection wires can be stably disposed in the bracket 850 using the guide protrusions 851.

Furthermore, an insert slot is formed in the outer surface of the upper end of the bracket 850, such that the bracket 850 can be securely coupled to other components.

Meanwhile, the main air washer body includes the blower 900, which draws indoor air into the housing, the disk assembly 600, which settles foreign substances, contained in the drawn air, in water and thus removes the foreign substances from the air, and the drive unit 1000, which operates the blower 900 and the disk assembly 600.

The blower 900 serves to forcibly draw air into the air inlet ports 401 using the blower fan 910, which is provided in the casing 920 of the intermediate body 320, to transport the air into the intermediate body 320 through the through hole of the casing 920, and to forcibly discharges the air outside the air washer through the air outlet ports 321. The blower fan 910 is supplied with rotating force from a blower motor 930.

Figure 7:
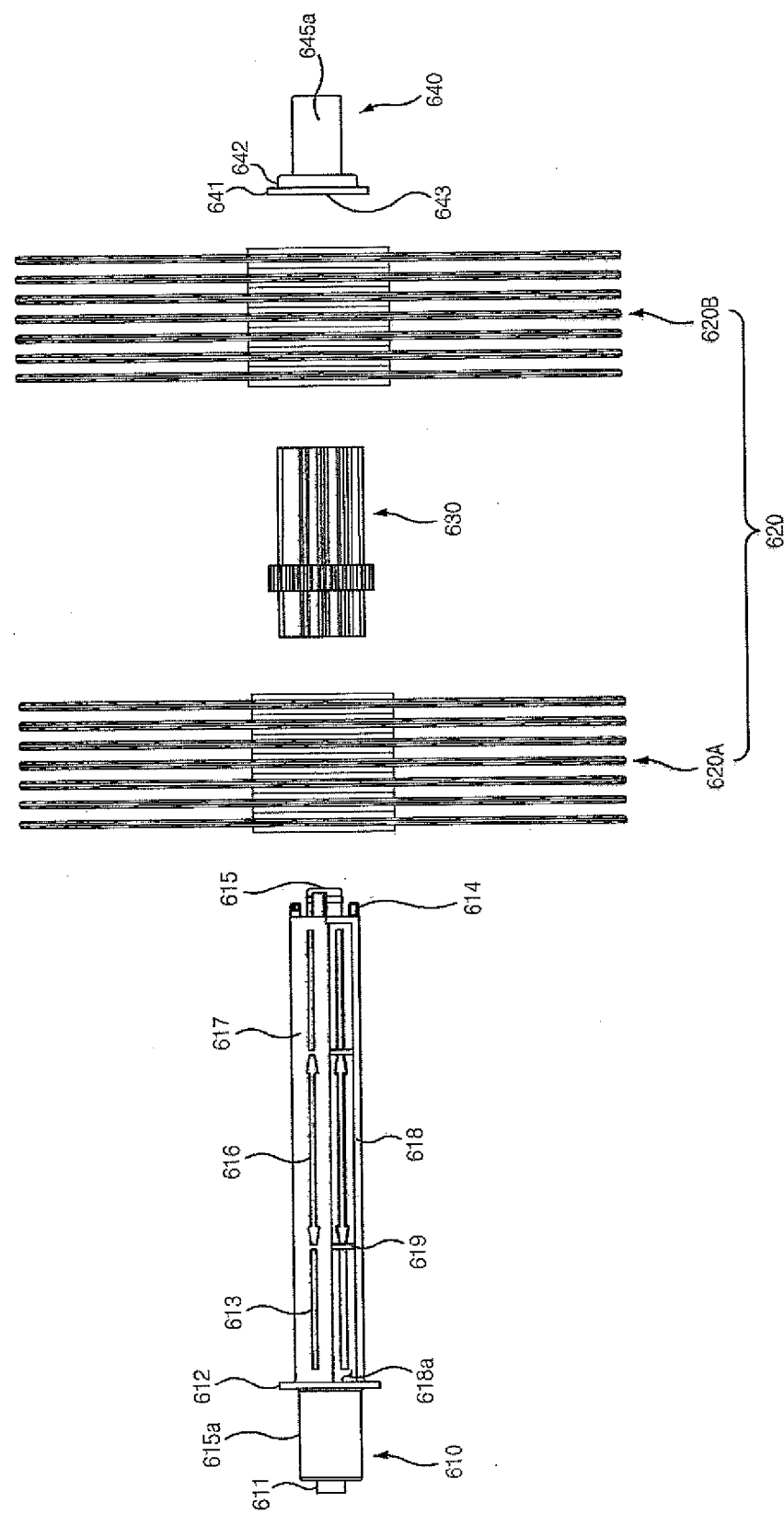
FIG. 7 is an exploded side view of a disk assembly of the air washer according to the present invention.
Figure 8:
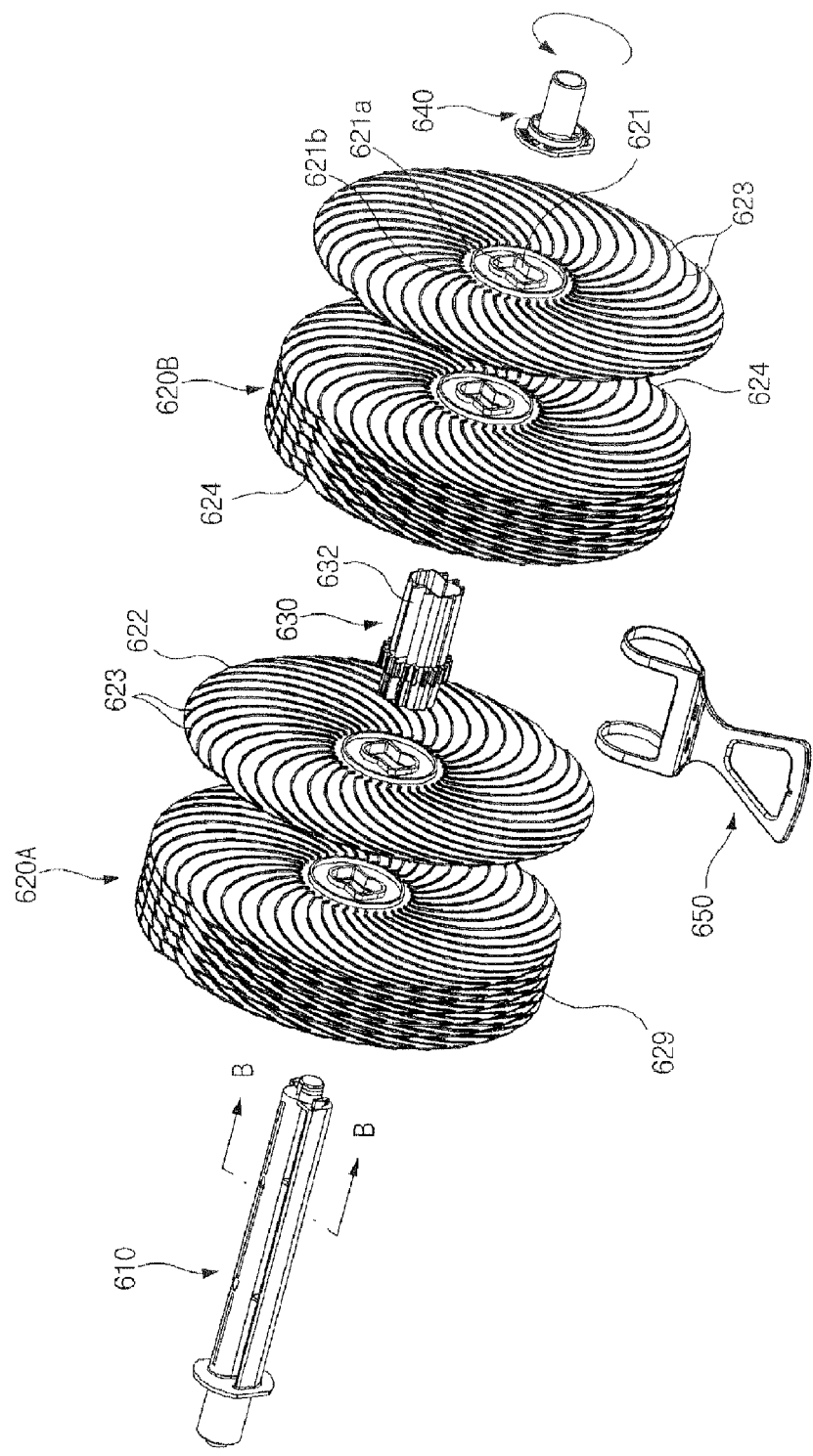
FIG. 8 is an exploded perspective view of the disk assembly of FIG. 7.
Figure 9:
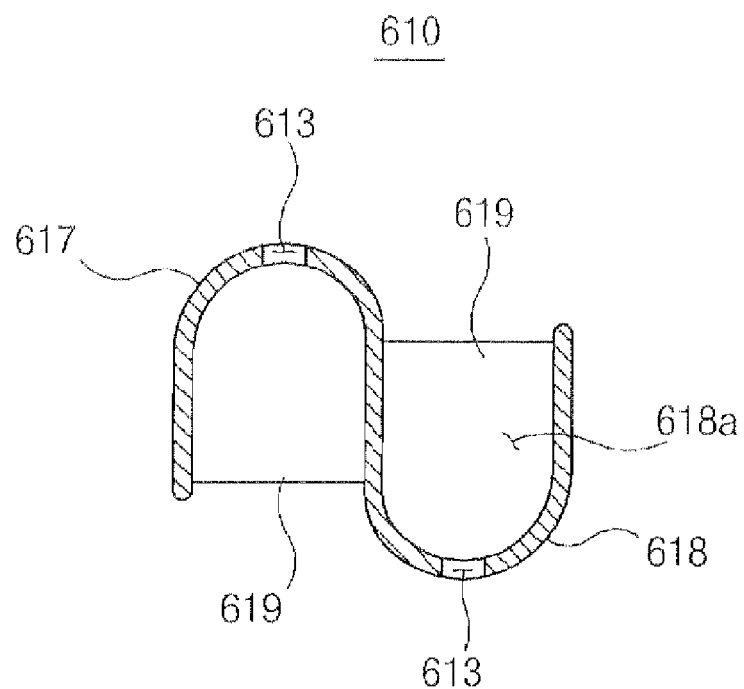
FIG. 9 is a sectional view taken along the line B-B of FIG. 8.
Figure 10:
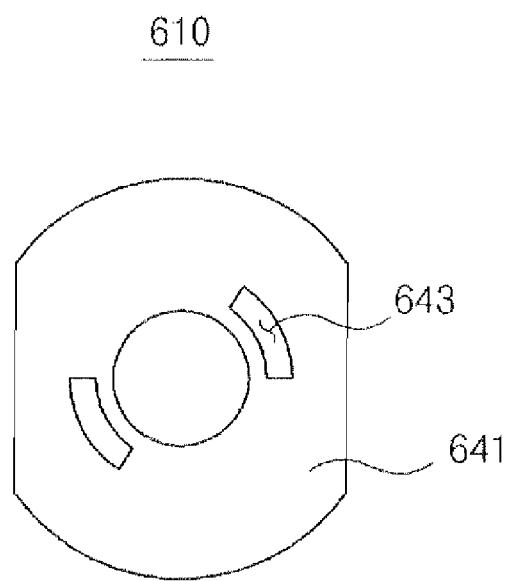
FIG. 10 is a bottom view of a cap of the air washer according to the present invention.

As shown in FIGS. 7 and 8, the disk assembly 600 includes a disk shaft 610, which has a stop ring 612 on one end thereof, the disks 620, which are fitted over the disk shaft 610, and an end cap 640, which is fitted over the other end of the disk shaft 610.

The disks 620 are divided into a first disk set 620A and a second disk set 620B, each of which has a plurality of disks. Each disk 620 draws up water, contained in the water reservoir 100, by rotating, thus forming a water film on the outer surface thereof. The water film, which is formed on the disk 620, adsorbs drawn air, and, when it is immersed by rotation of the disk 620 into the water in the water reservoir 100 again, foreign substances, which have been contained in the air, are transferred to the water. To increase the efficiency of this operation, arc-shaped ribs 623 are preferably provided on the surface of the disk 620 in a pinwheel-shaped arrangement. As such, a large number of ribs 623 is arranged between the center of the disk 620 and the outer edge thereof in an approximately radial direction.

The opposite ends of the disk shaft 610 comprise support shafts 645a and 615a, which are respectively seated into and supported by shaft seats 111 and 114 of the water reservoir 100.

Preferably, the support shaft 645a of the first end of the disk shaft 610 has a different shape from that of the support shaft 615a of the second end of the disk shaft 610. As such, because the support shafts 615a and 645a are differently shaped from each other, the support shaft 645a can be seated only into the shaft seat 111, while the support shaft 615a can be seated only into the shaft seat 114, thus preventing the ribs 623 from being rotated in the wrong direction. If the ribs 623 are rotated in the wrong direction, the operation of drawing up water is unsatisfactorily conducted. Thereby, the contaminant settling efficiency and air humidifying efficiency of the air washer is markedly reduced. In addition, due to poor rotation of the disk shaft 610, the lifetime thereof may be reduced.

Figure 16:
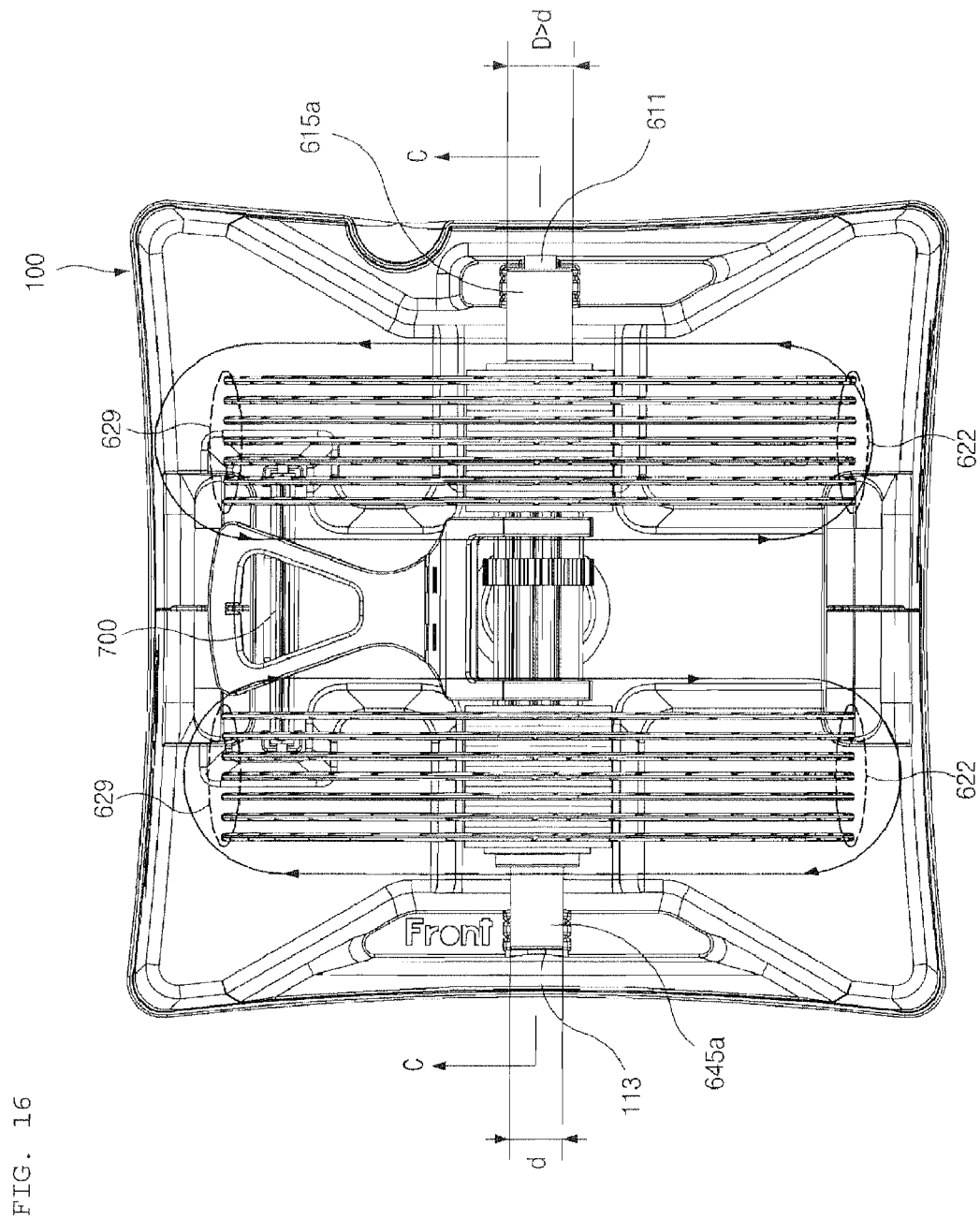
FIG. 16 is a plan view showing the disk assembly supported in a water reservoir according to the present invention.
Figure 17:
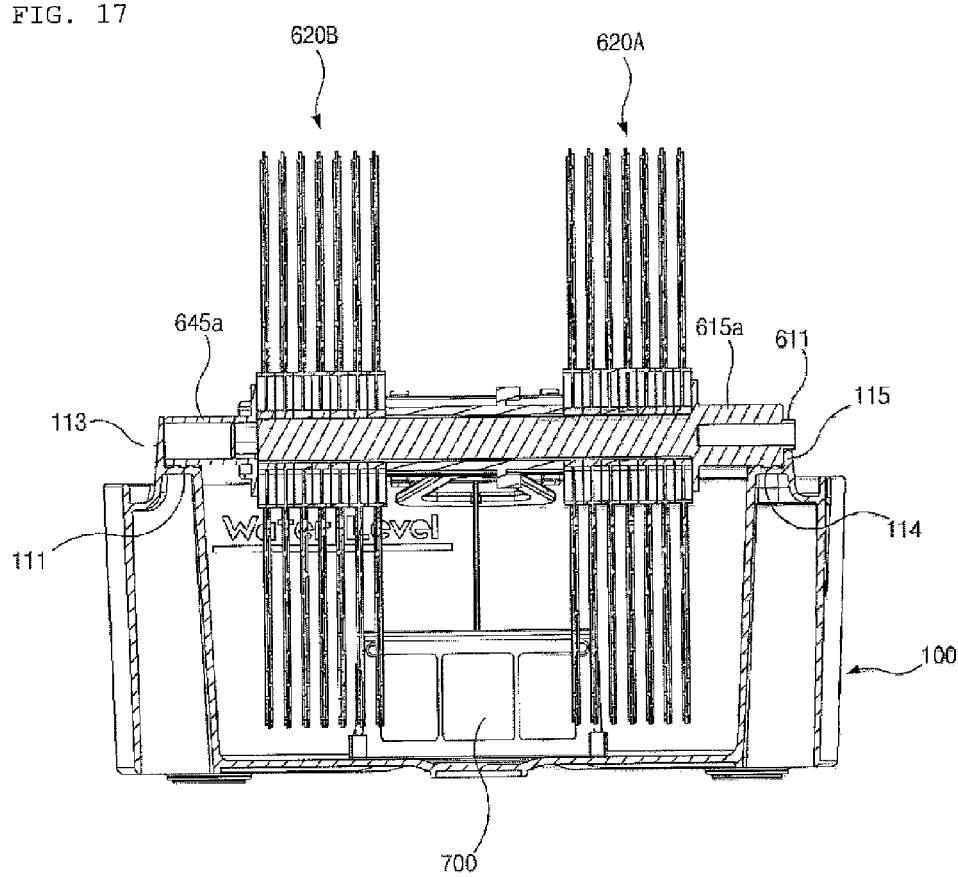
FIG. 17 is a sectional view taken along the line C-C of FIG. 16.

As a detailed example showing the asymmetrical shape, referring to FIGS. 16 and 17, the support shafts 615a and 645a may be constructed such that the diameter d of the support shaft 645a is less than the diameter D of the support shaft 615a. In this case, the shaft seats have structures such that they are differently shaped from each other, in the same manner as that of the support shafts. As such, thanks to the asymmetrical structure in diameter, if the disk shaft 610 is oriented in the incorrect direction, because the support shaft 615a, having a large diameter, cannot be inserted into the shaft seat 111, having a small diameter, the disk shaft 610 is prevented from being fitted in the wrong direction.

Furthermore, slide rings 112 are provided in the shaft seats 111 and 114, so that frictional resistance between the support shafts 615a and 645a and the shaft seats 111 and 114 is markedly reduced.

Meanwhile, as a detailed example showing the asymmetrical construction, the support shafts 615a and 645a may be constructed such that one support shaft is shorter than the other shaft. For example, this may be realized by a structure such that a support protrusion 611 is provided on the end of the support shaft 615a, as shown in FIGS. 16 and 17, so that the support shaft 615a is longer than the support shaft 645a by the length of the support protrusion 611. In this case, the support protrusion 611 is preferably seated into and supported by a separate protrusion seat 115.

Furthermore, to more reliably prevent incorrect assembly, in which the orientation of the disk shaft is incorrect, it is preferable that a stop piece 113 be provided in the shaft seat 111. In this case, even if the support protrusion 611 is intended to be seated into the shaft seat 111, because the support protrusion 611 interferes with the stop piece 113, incorrect assembly can be fundamentally prevented.

In addition, as shown in FIG. 4, it is preferable that the support protrusion 611 is coupled to the support shaft 615a using coupling ribs 601, so as to reduce the weight, thus reducing the load for rotation thereof.

Furthermore, as shown in FIGS. 4 and 17, preferably, the support protrusion 611 and the support shafts 615a and 645a have a pipe shape. In this case, even if the end of the support shaft 615a contacts the surface of the sidewall in which the protrusion seat 115 is defined, or even if the end of the support shaft 645a contacts the inner surface of the stop piece 113, because the area with which the end of the support shaft 615*a* or 645*a* contacts the corresponding contact surface, is small, frictional resistance therebetween can be reduced when the disk assembly 600 is rotated.

The disk shaft 610 has a rod shape, and the stop ring 612 is provided on the circumferential outer surface of the first end of the support shaft 615*a*.

Furthermore, a stepped protrusion 615 is provided on the second end of the disk shaft 610. The stepped protrusion 615 has a diameter smaller than that of the other part of the disk shaft 610, such that the cross-sectional area thereof is reduced. A groove is formed in the circumferential outer surface of the stepped protrusion 615 in the longitudinal direction of the disk shaft 610. An external thread may be formed on the circumferential outer surface of the stepped protrusion 615.

In addition, mounting protrusions 614 are provided on the second end of the disk shaft 610 at positions adjacent to the stepped protrusion 615. In this embodiment, the two mounting protrusions 614 are disposed on opposite sides of the stepped protrusion 615. Each mounting protrusion 614 is bent in a circumferential direction to have an 'L' shape.

In other words, a first end of each mounting protrusion 614 is coupled to the second end of the disk shaft 610, and a second end thereof is bent such that it is spaced apart from the surface of the disk shaft 610.

The stop ring 612 has a flange shape such that it extends around the entire circumference of the disk shaft 610.

Part of the disk shaft 610 between the stop ring 612 and the stepped protrusion 615 has a cross-section shaped such that it is asymmetrical based on the horizontal line passing through the center thereof and such that it is asymmetrical based on the vertical line passing through the center thereof. As such, because the disk shaft 610 has an asymmetric structure, the disks 620 can be fitted over the disk shaft 610 only in the correct direction. That is, even if it is attempted to fit the disks 620 over the disk shaft 610, the disks 620 cannot be fitted over the disk shaft 610.

Therefore, because the cross-section of the part of the disk shaft 610 over which the disks 620 are fitted has the above-mentioned shape, when a user couples the disks 620 and the disk shaft 610, which have been disassembled from each other to clean the disks 620, to each other, the disks 620 are prevented from being fitted over the disk shaft 610 in the wrong direction, in which the front and rear surfaces of the disks are oriented in the opposite direction.

Furthermore, because the disks 620 are prevented from being assembled in the wrong direction, even if the disks 620 are disassembled from and reassembled with the disk shaft 610, the ribs 623, which are formed on the disks 620, can always be oriented in the correct direction, thus maintaining the structure such that the ribs 623 can effectively draw up water from the lower housing 100.

Moreover, preferably, the disk shaft 610 is shaped such that the above-mentioned cross-section thereof is symmetrical based on a line in the diagonal direction. Thus, when the disks 620 are placed on the support surface in a state in which they are fitted over the disk shaft 610, the disks 620 are balanced and thus maintain the stationary state.

The disk shaft 610 is not limited to any particular shape, so long as it satisfies the above-mentioned conditions.

In this embodiment, the cross-section of the disk shaft 610 has at the upper end thereof a first convex part 617, which is convex upwards, and has at the lower end thereof a second convex part 618, which is convex downwards, that is, in the direction opposite the direction in which the first convex part 617 is convex. In other words, the cross-section of the disk shaft 610 generally has an 'S' shape.

Here, the first and second convex parts 617 and 618 are constructed such that inner ends thereof are connected to each other.

Between the stop ring 612 and the stepped protrusion 615 of the disk shaft 610, depressions 618*a* are respectively defined above the second convex part 618 and below the first convex part 617 in the longitudinal direction of the disk shaft 610.

Each depression 618*a* is formed in a curved shape corresponding to the shape of each of the first and second convex parts 617 and 618.

Two or more ribs 619 are provided in each depression 618*a* in lateral directions of the disk shaft 610.

The ribs 619, which are provided in the disk shaft 610, are disposed around respective boundary lines, by which the disks 620 are fitted over the disk shaft 610. That is, the ribs 619 are disposed opposite each other based on the medial portion of the disk shaft 610.

Furthermore, two through slots 613, which communicate with each depression 618*a*, are formed in the disk shaft 610 at opposite positions between the stop ring 612 and the stepped protrusion 615.

Thus, even though water enters the disk shaft 610, the water can flow out of the disk shaft 610 through the through slots 613 rather than remaining therein.

Meanwhile, indicators 616 are provided between the opposite through slots 613. That is, the indicators 616 are disposed in the medial portion of the disk shaft 610.

The indicators 616 serve to indicate the boundary lines, by which the disks 620 are fitted over the disk shaft 610.

The indicators 616 can be embodied by various methods such as printing. In this embodiment, each indicator 616 is embodied by a slot, which has arrow shapes at opposite ends thereof.

That is, two slots are formed to embody the indicators 616 such that they communicate with the respective depressions 618*a*, in the same manner as that of the through slots 613.

Such indicators 616 can also serve to drain water from the disk shaft 610 as well as having a function of indicating the boundary lines. Furthermore, because the indicators 616 are embodied by the slots, even when the disk shaft 610 is rotated, the user can easily observe the indicators 616 from any direction.

Meanwhile, a fitting hole 621 is formed through each disk 620, so that the disk 620 is fitted over the disk shaft 610 through the fitting hole 621. The fitting hole 621 has a shape corresponding to the cross-section of the disk shaft 610, and is formed in the center of the disk 620. That is, the fitting hole 621 has a generally rectangular shape and has arc-shaped curved parts at the top right hand corner and at the bottom left hand corner.

The two groups of disks 620 are fitted over the disk shaft 610 at opposite positions such that each group of disks 620 reaches each of the opposite ends of the indicators 616.

Furthermore, inner rims 621*a*, which surround the fitting hole 621, are formed on the front and rear surfaces of each disk 620.

As such, because the disk 620 has the inner rims 621*a*, the disk 620, which may be reduced in strength due to the formation of the fitting hole 621, can be reinforced. Furthermore, when the disk 620 is fitted over the disk shaft 610, the contact area between the disk 620 and the disk shaft 610 is increased, so that the disk 620 is prevented from being inclined in one direction, in other words, the disk 620 can stably maintain the state in which it is coupled to the disk shaft 610.

Furthermore, circular outer rims 621b, which surround the fitting hole 621, are provided on the front and rear surfaces of each disk 620 at positions spaced apart from the respective inner rims 621a. That is, the outer rims 621b are disposed between the fitting hole 621 and the ribs 623. The circular outer rims 621b serve to maintain constant intervals, at which the disks 620 are spaced apart from each other, when the disks 620 are fitted over the disk shaft 610.

The ribs 623 may be provided only on the front or rear surface of each disk 620 or, alternatively, may be provided on both the front and rear surfaces thereof. In the case where the ribs 623 are provided on both the front and rear surfaces of the disk 620, the ribs 623 are arranged such that the upper ends of the ribs 623 on the front surface of the disk 610 are not aligned with the upper ends of the ribs 623 on the rear surface thereof.

The disk assembly 600 has a rolling prevention means for preventing the disk assembly 600 from undesirably rolling on the support surface when the disk assembly 600 is separated from the water reservoir 100 and is placed on the support surface to, for example, clean the air washer.

As a representative example of the rolling prevention means, in this embodiment, rolling prevention cuts 624, each of which has an arc shape and is curved at a predetermined curvature, are formed in the outer edge of each disk 620 at opposite positions.

As well as the rolling prevention cuts 624, the rolling prevention means may be realized by protrusions, which protrude outwards from the outer edge of the disk 620, or by cutting parts of the outer edge of the disk 620, to have linear shapes.

Meanwhile, a stopper 627 is formed on the inner end of each rib 623, which is adjacent to the center of the disk 620.

The stopper 627 has a circular shape and protrudes from the rib 623 in a direction towards a tangent line of the circular outer rim 621b.

Each rib 623 has a curved part 625, which is convex in a direction opposite the direction in which the disk 620 is rotated. In addition, a bent part 626, which is bent to be convex in the direction opposite the direction in which the disk 620 is rotated, is formed in each rib 623 between the curved part 625 and the stopper 627. Thus, the rib 623 generally forms a hook shape.

Here, depending on the direction in which the disk 620 rotates, the shapes, in which the curved part 625 and the bent part 626 are curved and bent, may vary.

The bent part 626 is disposed at a position adjacent to the stopper 627, and is shorter than the curved part 625.

As well, a cut part 628 is formed in the outer end of each rib 623, which is adjacent to the outer edge of the disk 620, thus preventing the outer edge of the disk 620 from being sharpened. Thanks to the cut parts 628, the user is prevented from being injured by the pointed ends of the ribs 623 when cleaning the disk 620.

Meanwhile, in the disk assembly 600 of the present invention, the distance between the adjacent disks 620 is an important factor for enhancing the humidifying performance of the air washer. The distance between the adjacent disks 620 is determined by the height to which the inner rims 621a and the outer rims 621b protrude from the surface of the disk 620.

In this embodiment, the optimum distance between the adjacent disks 620 for enhancing the humidifying performance of the air washer was determined in the following test.

In a method of determining the optimum distance between disks in the disk assembly according to the present invention, after several models, which have various flow rates and flow rate uniformities depending on the distances between disks, are sampled, the model that has the largest number of disks, despite having relatively low flow rate uniformity, is determined as the optimum model.

Figure 28:
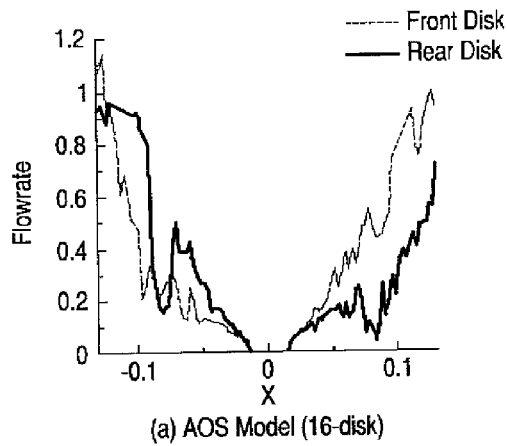
FIG. 28 is graphs showing flow rate distributions depending on distances between disks according to the present invention.
Figure 28:
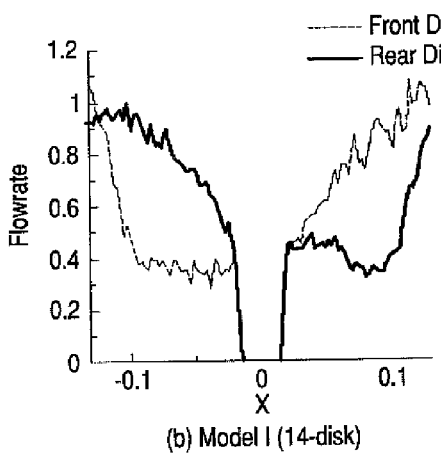
Figure 28:
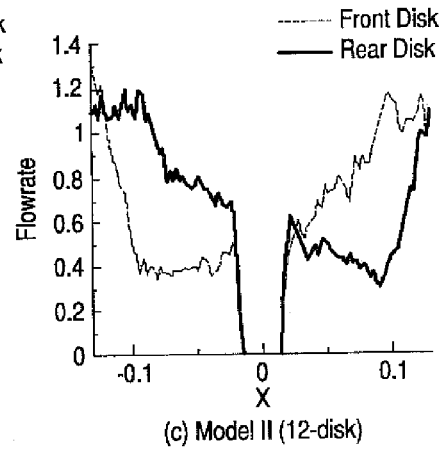
Figure 28:
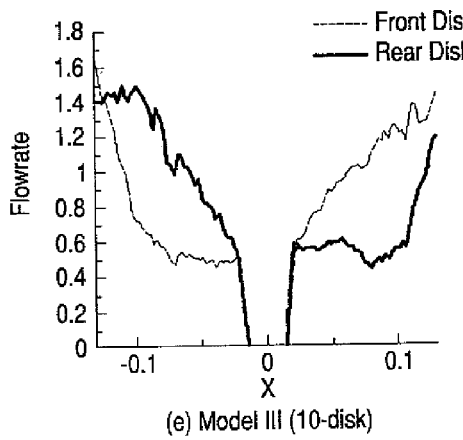
Figure 28:
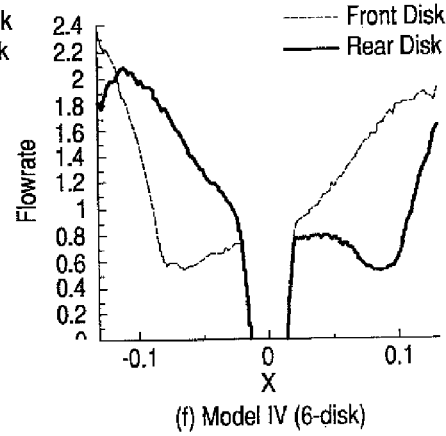
Figure 30:
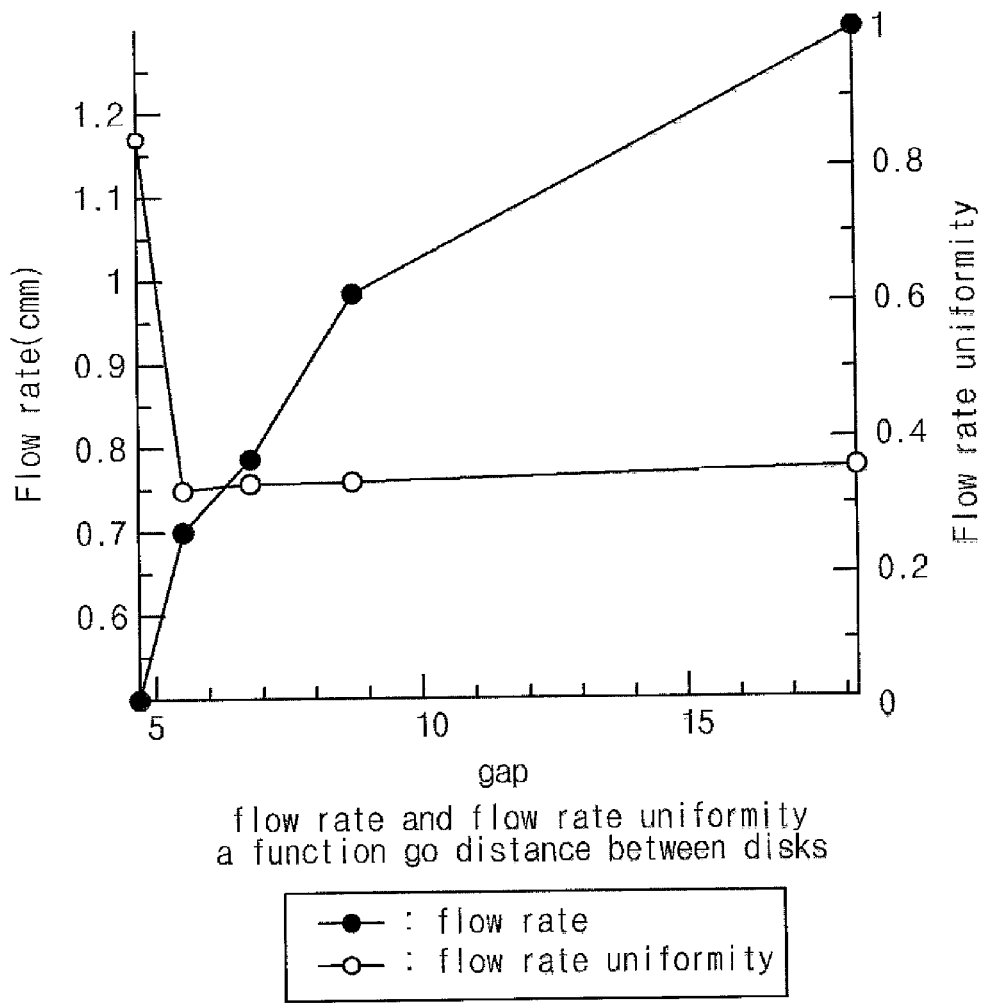
FIG. 30 is a graph showing flow rate and flow rate uniformity as a function of distance between the disks, according to the present invention.

FIG. 28 is graphs showing flow rate distributions depending on distances between adjacent disks, which are qualitatively deduced from several tests. FIG. 29 is a table showing the results of tests for flow rates and flow rate uniformity depending on the distance between adjacent disks. FIG. 30 is a graph showing the flow rate and the flow rate uniformity as a function of the distance between the adjacent disks.

Test models I through IV are samples used in the tests for determining the optimum design value of the distance between adjacent disks using a method in which the distance between adjacent disks is varied by changing the number of disks placed between a first disk and a last disk in a constant range, that is, in a state in which the distance between the first disk and the last disk is constant. Furthermore, the test models are improved models, which are proposed with the object of determining the optimum design value, at which an effective flow field, which can increase the efficiency with which air passing through passages defined between the disks is humidified, is formed between the disks.

In these tests, the humidifying efficiency is defined by the flow rate and the flow rate uniformity, and this is used to quantify the performances of the test models. Thus, the optimum design value is deduced by comparing the performances of the test models.

Furthermore, in these tests, the flow rate is defined by the amount of fluid passing through a cross-section of the passage between the disks, which is taken along the center line passing through the centers of the disks. In addition, to define the uniformity of the flow rate of fluid drawn between the disks, the flow rate uniformity k is defined by the following formula using the standard deviation of the flow rates at several positions on the center line of the one disk.

$$k = \sqrt{\frac{1}{N}\sum\left(\frac{\rho u_i - \rho \overline{U}}{\rho \overline{U}}\right)^2}$$

N: the number of measurement points, at which flow rates are measured
ρ: density of fluid (air)
U: mean velocity of air
$U_i$: velocity of air at measurement point The flow rate uniformity is a barometer indicating how constant the velocity distribution of air throughout the entire area of the disk is. The flow rate uniformity is indicated by the ratio of velocity of air at every measurement point to the mean velocity of air in the entire area of the disk.

Furthermore, in these tests, the flow rate uniformity is defined by the standard deviation of partial mass flow rates at measurement points in the X direction with respect to the mean mass flow rate between the disks. Here, as the flow rate uniformity approaches the value 1, this means that a very uneven flow field is formed between the disks. In contrast, as the flow rate uniformity approaches the value 0, this means that an even flow field is generally formed between the disks.

As shown in FIG. 28, showing the flow rate distribution between the disks, which is qualitatively deduced, in the case of a basic AOS model of Graph a, it is understood that the flow rate rapidly decreases around the central portion (x=0) of the disk, and that the flow rate greatly increases around the perimeter (x>+0.1) of the disk. This uneven flow rate deteriorates the humidifying performance of the air washer, because the natural evaporation ability using the flow of air is reduced.

Graph b shows the case of a model using fourteen disks, in which the number of disks is two less than that of the basic AOS model, that is, there is one less disk in the front part of the disk assembly and one less disk in the rear part thereof. In this case, as can be seen in Graph b, the flow rate is increased around the central portion (x=0) of the disk, compared to the basic AOS model.

Furthermore, Graphs c through e illustrate the flow rates of models having twelve, ten and six disks, respectively. As shown in Graphs c through e, it is appreciated that the qualitative shapes of flow rate distributions are similar to that of the basic AOS model, but, as the number of disks is reduced, the total flow rate is increased. This results from a reduction in the total area of surfaces for providing viscous force and from an increase in the total area of passages, through which fluid passes, because of a reduction in the number of disks.

Here, the humidification rate is determined by the natural evaporation rate, which pertains both to the amount of water applied to the surfaces of the disks and to the amount of air passing through the surfaces of the disks. Therefore, an increase in the flow rate does not always result in an increase in the humidification rate. Thus, in the present invention, in consideration of flow rate uniformity, it is preferable that a model that has a relatively large number of disks and yet maintains superior flow rate uniformity be determined to be the optimum model.

Meanwhile, in the Table of FIG. 29, showing flow rates and flow rate uniformities depending on the distance between the disks, the distance P between the disks of each model is as follows.

| |
|---|
| 16-disks → 6.0 mm |
| 14-disks → 6.8 mm |
| 12-disks → 8.0 mm |
| 10-disks → 9.6 mm |

Furthermore, detailed specifications, such as the pitch P, thickness T, gap G, etc., of each model are shown in the following Table 1.

TABLE 1

| Model | Disk Pitch (P) | Disk Thickness (T) | Disk Gap (G) | Rim Height (H) |
|---|---|---|---|---|
| 16-disks | 6.0 | 1.0 | 5.0 | 2.5 |
| 14-disks | 6.8 | 1.0 | 5.8 | 2.9 |
| 12-disks | 8.0 | 1.0 | 7.0 | 3.5 |
| 10-disks | 9.6 | 1.0 | 8.6 | 4.3 |

Unit: mm
Disk Pitch (P): distance between centers of adjacent disks
Disk Gap (G): distance between facing surfaces of adjacent disks (P-T)
Rim Height (H): height at which rim protrudes from surface of disk (P-T/2)

FIG. 30 is a graph showing the flow rate and the flow rate uniformity as a function of the distance between adjacent disks. The x-axis denotes the distance between adjacent disks, the y1-axis (left) denotes the flow rate, and the y2-axis (right) denotes flow rate uniformity. As shown in the graph of FIG. 30, in the 14-disks and 12-disks, although the distance between the disks is increased, flow rate uniformity does not vary greatly, but the flow rate is gradually increased. As stated above, because an increase in the flow rate does not always result in an increase in the humidification rate, in the present invention, the model 1 (14 disks) and the model 2 (12 disks), which maintain a superior flow rate uniformity despite having a relatively large number of disks, were determined to be the models having optimum design values in consideration of the distance between disks. Furthermore, from the above tests, the present invention is preferably designed such that the optimum distance between disks ranges from 6.5 mm to 8.6 mm.

Meanwhile, in the air washer of the present invention, a method of determining the optimum distance between disks in the disk assembly may be conducted in a manner different from the above-mentioned disk distance determining method. For example, several models having various flow rates and flow rate uniformities depending on the distances between disks are sampled. Thereafter, of the sampled models, a model, the flow rate uniformity of which is 0.35 or less, is determined as the optimum model.

Alternatively, as a method of determining the optimum distance between disks in the disk assembly, after several models, which have various flow rates and flow rate uniformities depending on the distances between disks, are sampled, a model that has a relatively large number of disks and has a flow rate uniformity of 0.35 or less may be determined as the optimum model.

Figure 22:
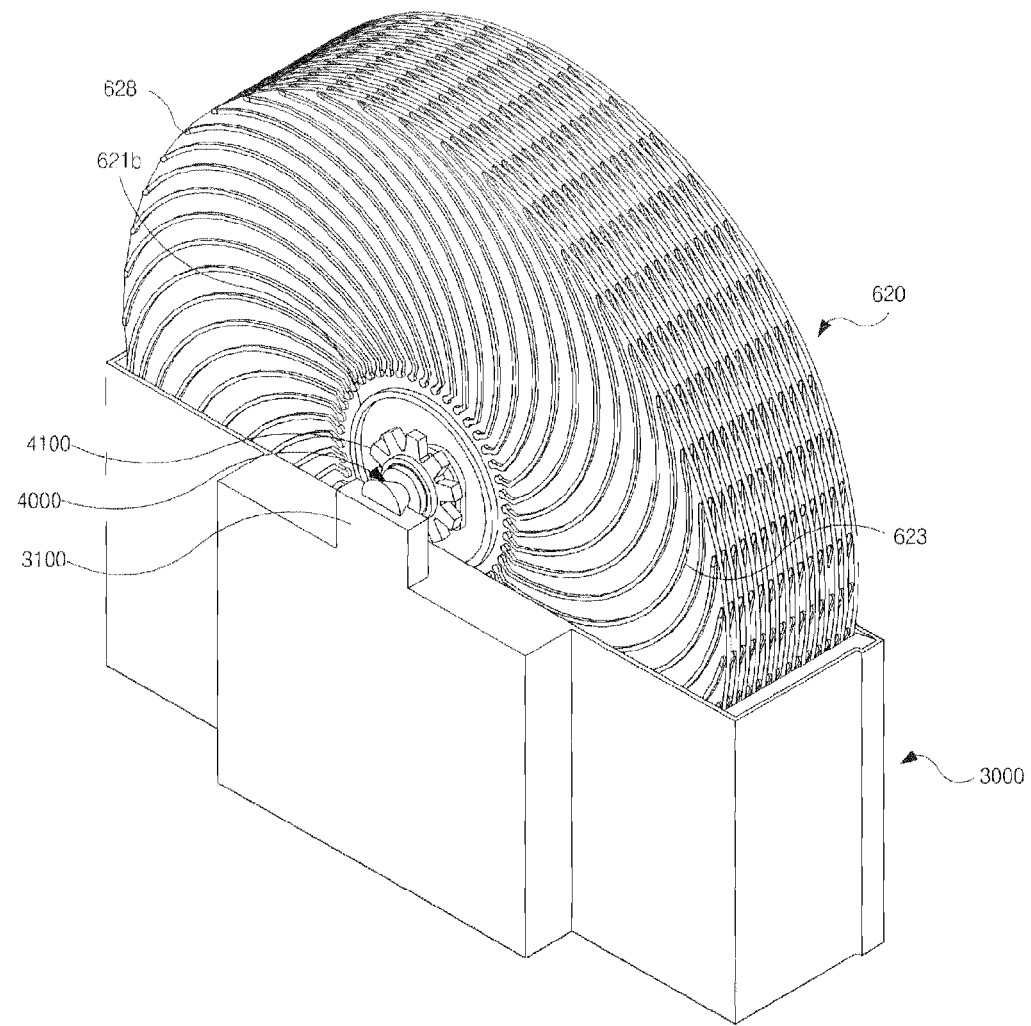
FIG. 22 is a perspective view of a disk assembly according to a modification of the embodiment of the present invention.
Figure 23:
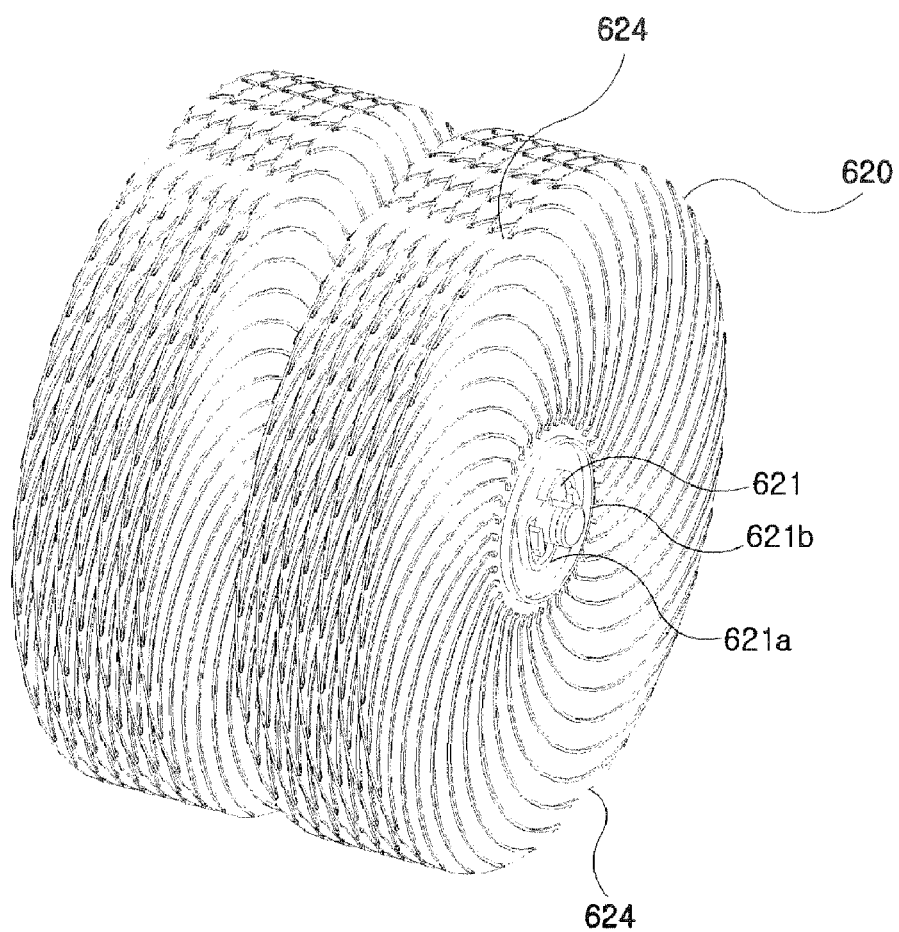
FIG. 23 is a detailed view of the disk assembly according to the present invention.

FIG. 22 is a perspective view of a disk assembly, according to a modification of the embodiment of the present invention.

In this case, a rotating shaft 4000 is inserted into fitting holes 621, which are formed through a large number of the disks 620.

A drive gear 4100 is provided on the front end of the rotating shaft 4000, and a ring-shaped coupling depression is formed in the rotating shaft 4000 ahead of the drive gear 4100.

A drive device (not shown), which rotates the drive gear 4100, includes a motor and an output gear, which is connected to an output shaft of the motor. The output gear engages with the drive gear 4100, so that the disks 620 are rotated.

The disks 620 are installed in a housing 3000, which serves as a water reservoir containing water therein.

The housing 3000 may consist of an upper housing and a lower housing. The lower housing contains water therein, and the upper housing serves as a cover.

The housing 3000 may be constructed such that opposite sidewalls thereof are inclined to form a shape corresponding to the shape of the disks 620 to minimize space for installation of the housing 3000.

Furthermore, a support protruding part 3100 is provided on the front surface of the lower housing of the housing 3000.

The support protruding part 3100 protrudes upwards from the upper surface of the lower housing to a height corresponding to the positions of the fitting holes 621 of the disk 620.

The support protruding part 3100 has therein a shaft seat, into which the rotating shaft 4000 is seated. In addition, the support protruding part 3100 has a coupling stop, which is inserted into the ring-shaped coupling depression of the rotating shaft 4000 when the rotating shaft 4000 is seated into the shaft seat.

Furthermore, a seating groove for preventing the rotating shaft 4000 from being undesirably removed is formed in the coupling stop.

As such, the disks 620 and the rotating shaft 4000 are rotatably installed in the housing 3000.

In this embodiment, having the above-mentioned construction, when the drive device is operated, the rotating shaft 4000 is rotated by the driving force of the drive device, so that the disks 620 are rotated along with the rotating shaft 4000.

As such, when the disks 620, which are constructed such that parts thereof are immersed in water, are rotated, ribs 623 of the disks 620, which have been immersed in the water, are removed from the water. At this time, water is drawn up by the curved parts 625 of the disks 620. When the disks 620 are further rotated, water, which has been drawn up by the curved parts 625 of the ribs 623, flows downwards. Here, water remains for a while in the inner ends of the ribs 623 by bent parts 626 and stoppers 627, which are provided on the inner ends of the ribs 623, rather than directly falling down from the ribs 623.

Therefore, compared to the conventional art, an increased amount of water can be applied to each disk 620 for an increased time. Thus, there is an advantage in that the humidification efficiency of the air washer is increased.

Meanwhile, in the present invention, a spacer 630, which has a hollow pipe shape, is fitted over the disk shaft 610 between the first disk set 620A and the second disk set 620B. Here, a through hole, which is formed through the spacer 630, corresponds to the shape of the cross-section of the disk shaft 610.

Furthermore, gear teeth 631 are formed around the circumferential outer surface of the spacer 630. The gear teeth 631 engage with a drive gear 530 of a disk motor 510. The gear teeth 631 are disposed at an eccentric position adjacent to one end of the spacer 630 so as to enhance the provision of space for installation of the disk motor 510.

In addition, reinforcing ribs 632 are provided on the circumferential outer surface of the spacer 630 in the longitudinal direction of the spacer 630. The reinforcing ribs 632 are disposed at opposite sides of the gear teeth 631 and serve to reinforce the strength of the spacer 630.

The spacer 630 having the above-mentioned structure serves to maintain a constant distance between the first and second disk sets 620A and 620B and to transmit rotating force from the disk motor 510 of a disk drive unit 500 to the disk shaft 610.

The end cap 640 has a cylindrical shape and is fitted over the stepped protrusion 615, which is provided on the second end of the disk shaft 610. A flange 641 is provided around the circumferential outer surface of the end cap 640. Insert slots 643 are formed in the flange 641 such that the mounting protrusions 614 of the disk shaft 610 can be fitted into the insert slots 643. In the present invention, the two insert slots 643 are formed at opposite sides of the center of the flange 641, and each insert slot 643 extends a predetermined length in a circumferential direction.

In addition, a stepped stop 642 is provided around the end cap 640 at a position adjacent to the flange 641, such that the flange 641 and the stepped stop 642 are stepped with respect to each other. Here, the stepped stop 642 is disposed at a position spaced apart from the flange 641 such that a space is defined between the stepped stop 642 and the flange 641.

This space communicates with the insert slots 643. As well, a through hole is formed through the upper surface of the stepped stop 642, such that the through hole communicates with the space defined between the stepped stop 642 and the flange 641, so that the interior of the stepped stop 642 can be observed from the outside.

As such, thanks to the through hole of the stepped stop 642, when the disk assembly is assembled, positions of the mounting protrusions 614 that are disposed between the stepped stop 642 and the flange 641 can be easily observed, thus making the assembly process easy.

Furthermore, an internal thread is formed in the circumferential inner surface of the end cap 640. Thus, the end cap 640 is coupled to the stepped protrusion 615 of the disk shaft 610 by screw coupling.

To assemble the disk assembly 600 having the above-mentioned construction, the first disk set 620A is fitted over the disk shaft 610 by the position at which the left end of the indicator 616 is disposed. Thereafter, the spacer 630 is fitted over the disk shaft 610, and the second disk set 620B is fitted over the disk shaft 610. Subsequently, the end cap 640 is fitted over the stepped protrusion 615 of the disk shaft 610, and, simultaneously, the mounting protrusions 614 are inserted into the insert slots 643 of the flange 641. Thereafter, when the end cap 640 is rotated, the mounting protrusions 614 are seated into the space between the stepped stop 642 and the flange 641, thus completing the assembly process. Here, the mounting protrusions 614 are prevented from being moved by the stepped stop 642 and the flange 641, thus maintaining the fixed state.

As such, in the present invention, because the disks 620 are fitted over the disk shaft 610 in one direction and the end cap 640 is coupled to the disk shaft 610 in the same direction, the number of man-hours required for the assembly process is reduced, thus making the assembly process easy.

Figure 11:
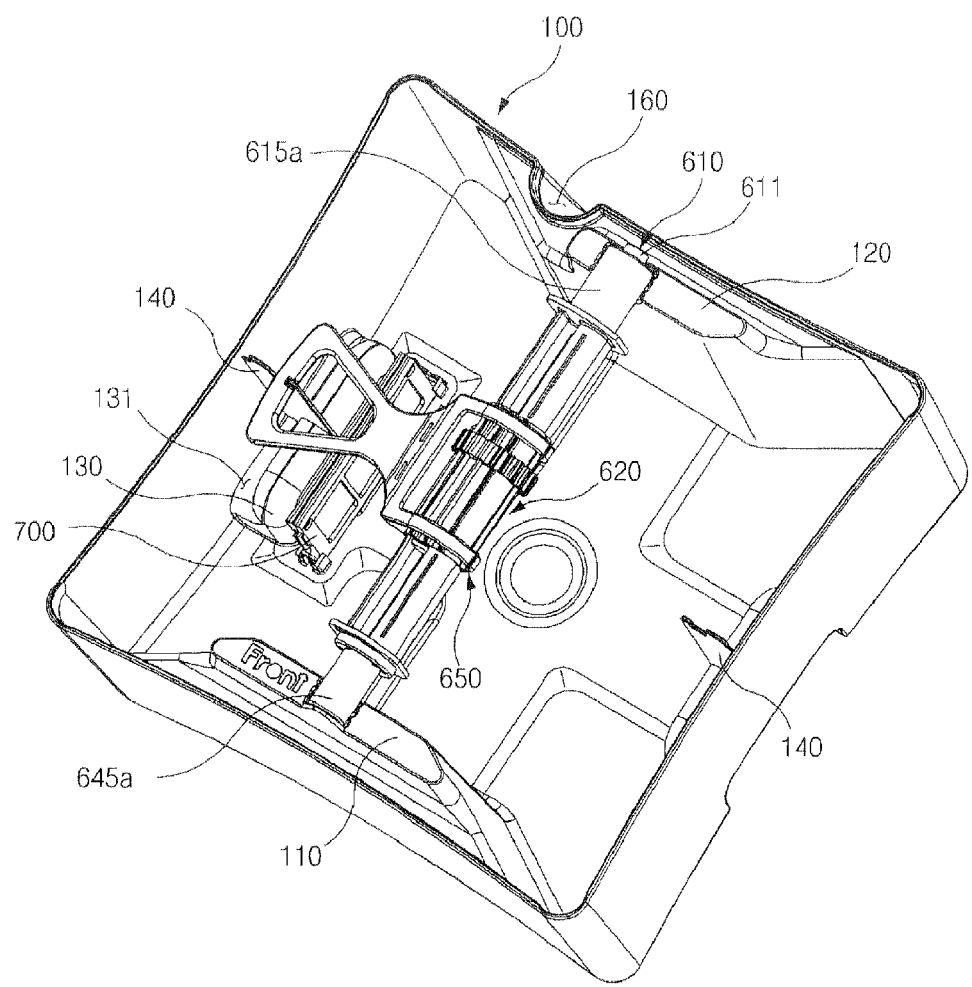
FIG. 11 is a view showing the installation of a disk shaft handle of the air washer according to the present invention.
Figure 12:
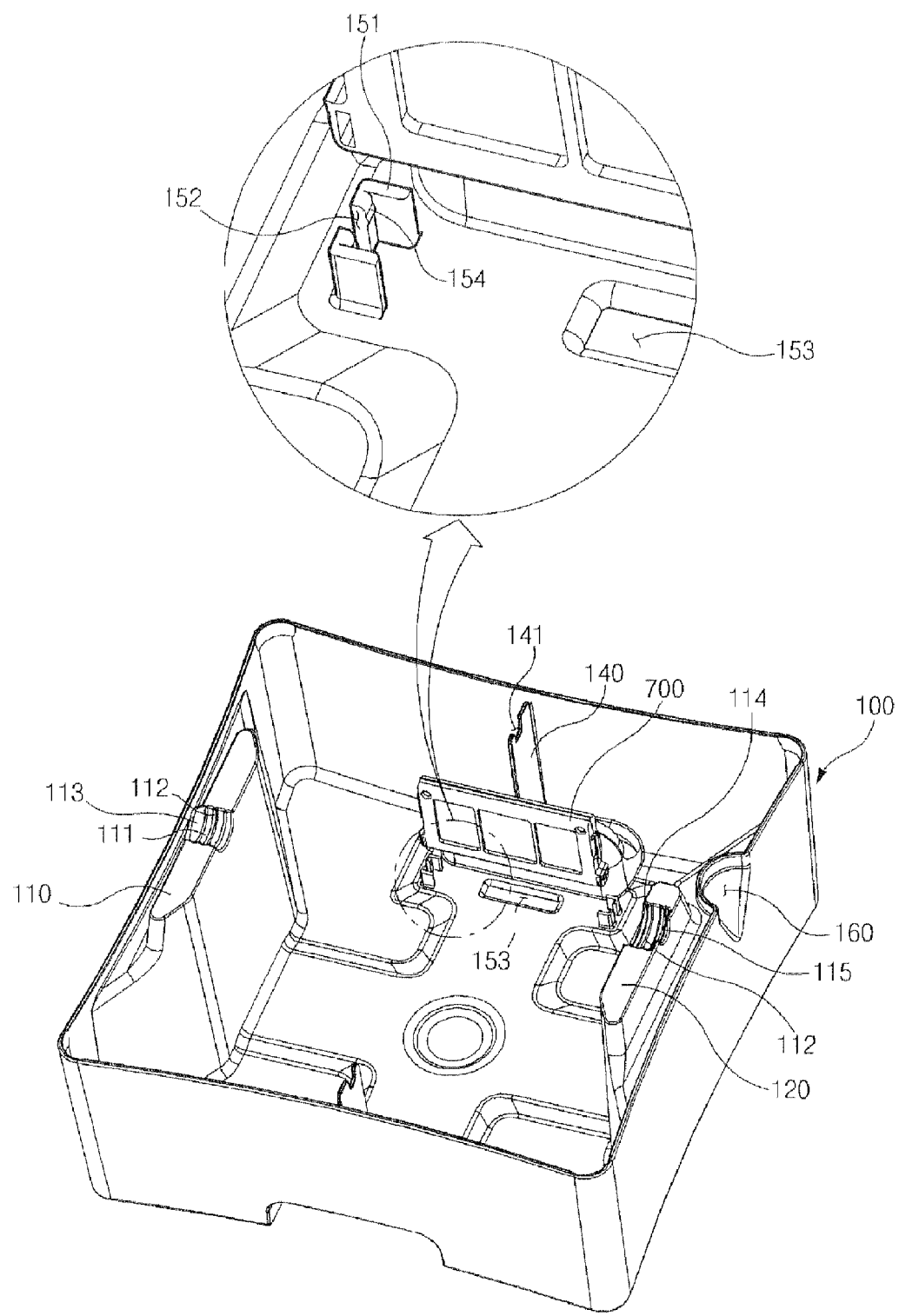
FIG. 12 is a partially enlarged perspective view of a lower housing of the air washer according to the present invention.

Meanwhile, as shown in FIGS. 11 and 12, the lower housing 100 is the water reservoir 100, which includes the bottom and the sidewalls, which surround the bottom. The lower housing 100 has a rectangular shape. A first support 110, which has the shaft seat 111 therein, and a second support 120, which has the shaft seat 114 and the protrusion seat 115 therein, are provided in the lower housing 100 at positions adjacent to the respective front and rear walls thereof in lateral directions, that is, along the front and rear walls. The first support 110 and the second support 120 are formed by protruding the bottom of the lower housing 100 upwards. That is, they are formed by a method similar to a method of forming a structure having a cap shape through a drawing process.

Therefore, depressions are formed in lower surfaces of respective parts of the bottom of the lower housing 100, in which the first support 110 and the second support 120 are formed. The depressions may be used as a handle when carrying the air washer.

Each of the first support 110 and the second support 120 has a support boss, which protrudes at a position spaced apart from the corresponding sidewall of the lower housing 100. The support boss protrudes to a position higher than the sidewalls of the lower housing 100.

Furthermore, an indication mark for indicating the front and rear of the air washer is formed on the support boss of the first support 110.

In addition, the support boss of the second support 120 of the lower housing 100 serves to support the switching bar 830 of the switch 800.

Support ribs 140 are provided on the inner surfaces of the respective left and right sidewalls of the lower housing 100. Each support rib 140 has a planar shape and is oriented in a vertical direction perpendicular to the corresponding sidewall of the lower housing 100.

A handle seat 141 is formed in the upper edge of each support rib 140.

Here, part of the support rib 140, onto which a grip part 656 is seated, has an inclined edge.

For this, the handle seat 141 has a shape such that the depth thereof is increased towards the outside of the lower housing 100. Thanks to the handle seat 141 having this shape, the disk shaft handle 650, which is placed in the lower housing 100 and has a predetermined inclination, can be stably seated into the handle seat 141 of the support rib 140.

Furthermore, a notch, which is shallower than the handle seat 141, is formed between the upper end of each support rib 140 and the corresponding side wall of the lower housing 100.

Moreover, protruding parts 130 are provided on the inner surfaces of the respective left and right sidewalls of the lower housing 100 on the lower ends of the respective support ribs 140, and each protruding part 130 extends a predetermined length in a forward-backward direction, that is, along the corresponding sidewall of the lower housing 100.

Each protruding part 130 is formed by compressing the junction between the bottom and the outer surface of the corresponding sidewall of the lower housing 100 inwards. Thus, a depression is formed at the junction between the corresponding sidewall and the bottom of the lower housing 100. Such depressions may serve as handles to be held in the hands of the user when carrying the air washer. The protruding parts 130 may also be formed through drawing processes, in the same manner as that of the first and second supports 110 and 120.

Moreover, each depression is formed in an 'L' shape, so that space 131 is defined in the lower housing 100 between the corresponding sidewall thereof and the protruding part 130.

Meanwhile, a lead recess 160 is formed in the upper end of the rear wall of the lower housing 100. The lead recess 160 is reduced in width from the top thereof to the bottom. The power connection wire extends outside the air washer through the lead recess 160.

The lower housing 100 has mounting slots in the bottom thereof. In detail, as shown in FIG. 12, two installation protrusions 151 are provided on the bottom of the lower housing 100. The two installation protrusions 151 are oriented such that they face each other. The mounting slots are formed in the respective installation protrusions 151, such that they face each other.

Therefore, each installation protrusion 151 has a 'U' shape when seen in a plan view.

Furthermore, a cut slot 152 is formed in each installation protrusion 151 in the direction in which a receiving frame 700 is fitted into the installation protrusions 151. In other words, the cut slot 152 is formed in the vertical direction of the air washer. Furthermore, the cut slots 152 of the installation protrusions 151 communicate with the mounting slots.

Thus, when the receiving frame 700 is fitted between the installation protrusions 151 of the lower housing 100, the cut slots 152 of the installation protrusions 151 widen, that is, the installation protrusions 151 are elastically opened, so that the receiving frame 700, which is inserted into the mounting slots of the installation protrusions 151, can be securely held by the installation protrusions 151.

Furthermore, locking protrusions 154 are provided on the inner surface of the mounting slots, in other words, in the inner surfaces of the respective installation protrusions 151, in a horizontal direction.

In addition, a depression 153 extending a predetermined length is formed in the bottom of the lower housing 100 between the installation protrusions 151.

Meanwhile, a sterilizing unit includes a sterilizing chip (not shown), and a receiving frame 700, which removably receives the sterilizing chip. The sterilizing chip comprises a sterilizing substance such as a silver (Ag) net or a silver (Ag) ball and serves to prevent the propagation of bacteria in water in the lower housing 100.

Figure 18:
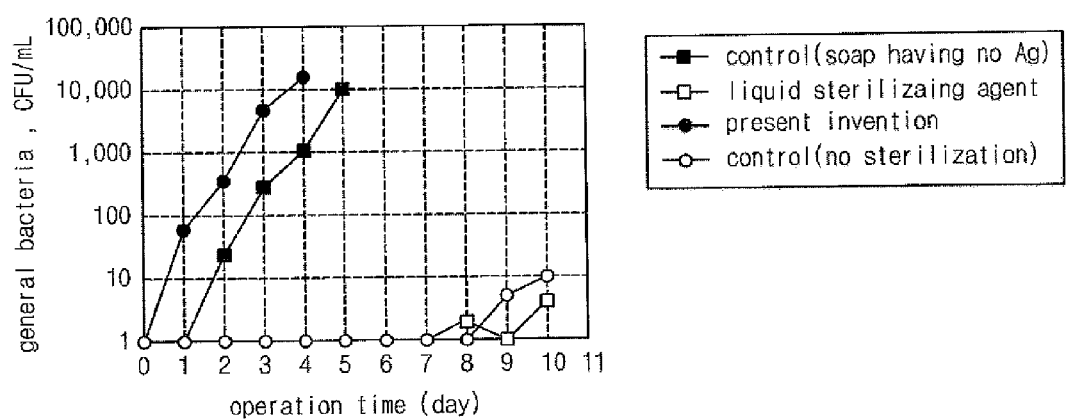
FIG. 18 is a graph showing the number of bacilli as a function of the operation period according to a sterilizing method in a vaporizing humidifier.

The sterilizing unit of the present invention is convenient, compared to that of the conventional art in which liquid sterilizing agent is mixed with water in the water reservoir, because only a process of replacing the sterilizing chip with a new one is required, without requiring a process of replacing all of the water in the water reservoir. Furthermore, as shown in FIG. 18, in a test, in the case of the sterilizing unit of the present invention, the propagation of bacteria was prevented until the eighth day after the commencement of operation of the air washer.

As shown in FIG. 16, preferably, the sterilizing unit is disposed between the first and second disk sets 620A and 620B at a position adjacent to front sides 629 of the disk sets 620A and 620B. Here, the front sides 629 are parts of the first and second disk sets 620A and 620B which are immersed in water when the disk sets 620A and 620B are rotated, and rear sides 622 are parts of the first and second disk sets 620A and 620B which are removed from water, and thus draw up water, when they are rotated.

Therefore, when the disk assembly 600 is rotated, as shown in FIG. 16, waves of water begin from the front sides 629 and water currents are generated in the directions indicated by the arrows. Because these water currents first contact the sterilizing unit, sterilizing substances can be smoothly drawn out of from the sterilizing unit, and the sterilizing substances can be evenly dispersed in water in the water reservoir 100.

Figure 13:
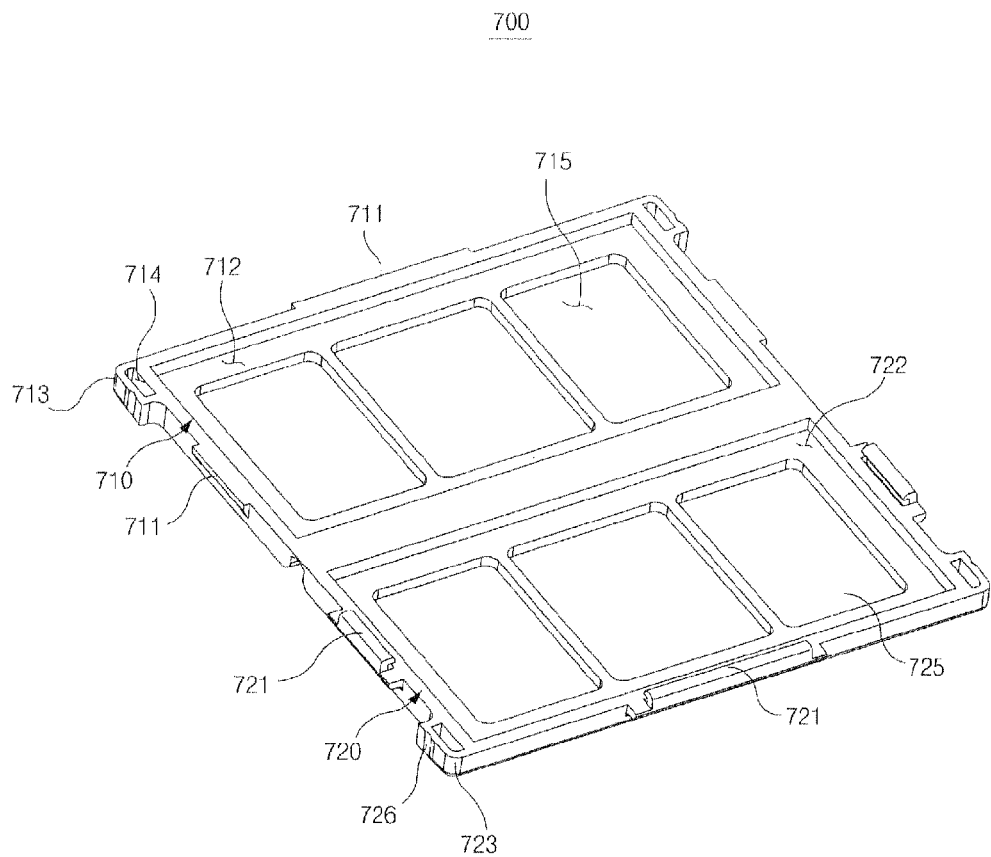
FIG. 13 is a perspective view of a casing of a sterilizing means of the air washer according to the present invention.

As shown in FIG. 13, the receiving frame 700 includes a frame body, which consists of a first plate 710 and a second plate 720. A receiving space is defined between the first plate 710 and the second plate 720, and openings 715 and 725, which communicate with the receiving space, are formed in the first and second plates 710 and 720.

The receiving frame 700 is fitted into the mounting slots defined in the lower housing 100.

The first plate 710 and the second plate 720 have planar shapes, and receiving depressions 712 and 722 are formed in facing surfaces of the respective first and second plates 710 and 720.

The receiving depressions 712 and 722 define the receiving space, and the sterilizing chip is seated in the receiving space.

The first and second plates 710 and 720 may be manufactured into a single body. In this case, the junction between the first and second plates 710 and 720 is thinner than the other parts to function as a film hinge, so that the first and second plates 710 and 720 are connected to each other so as to be rotatable around the film hinge, that is, the junction therebetween.

Alternatively, the first and second plates 710 and 720 are separately provided. The first and second plates 710 and 720, having the above-mentioned structures, may be coupled to and locked to each other by coupling between catches 711, which are provided in the first plate 710, and locking hooks 721, which are provided in the second plate 720.

As such, because the receiving frame 700 has a structure such that the first and second plates 710 and 720 are coupled to each other, it is convenient to store and maintain the receiving frame 700.

The three rectangular openings 715, 725 are formed in each of the first and second plates 710, 720.

The catches 711 protrude outwards from the opposite edges and the lower edge of the first plate 710.

Furthermore, the locking hooks 721, which are locked to the respective catches 711, are provided on the opposite edges and the lower edge of the second plate 720. Each locking hook 721 protrudes from the second plate 720 towards the first plate 710 at a position corresponding to the corresponding catch 711. In addition, each locking hook 721 has an inclined surface such that the thickness thereof is reduced towards the first plate 710. As such, because the receiving frame 700 is openably closed using the locking hooks 721 and the catches 711, the process of replacing the sterilizing chip with a new one can be easily conducted.

As well, insert protrusions 713 and 723 are provided on the opposite edges of the respective first and second plates 710 and 720, which are the frame body. In detail, the insert protrusions 713 and 723 are disposed on the opposite edges of the lower ends of the respective first and second plates 710 and

720. Furthermore, each insert protrusion 713, 723 is formed such that one surface thereof extends from the lower edge of each of the first and second plates 710 and 720 to be in the same plane. Locking grooves 726, into which the locking protrusions 154 of the installation protrusions 151 are engaged, are formed in the respective insert protrusions 713 and 723. Thanks to this structure, when the receiving frame 700 is mounted to the lower housing 100, it can be securely fastened to the lower housing 100 by the double locking structure.

Moreover, through holes 714 are formed in the receiving frame 700 at positions between the openings 715 and 725 and the locking grooves 726, for example, in the respective insert protrusions 713 and 723. The through holes 714 allow for the receiving frame 700 to elastically move when the receiving frame 700 is fitted into the mounting slots of the lower housing 100, thus preventing the receiving frame 700 from being undesirably deformed, and making it possible for the receiving frame 700 to be securely fitted into the mounting slots.

After the sterilizing chip, which is a sterilizing means, is placed in the receiving space defined in the receiving frame 700, the first plate 720 is rotated and the locking hooks 721 are locked to the respective catches 711. Then, the process of assembling the sterilizing chip with the receiving frame 700 is completed.

Thereafter, the receiving frame 700 having the sterilizing chip therein is disposed between the installation protrusions 151 above the depression 153. Subsequently, the receiving frame 700 is pushed downwards. Then, the insert protrusions 713 and 723 are inserted into the mounting slots of the installation protrusions 151, and the locking protrusions 154 are locked to the locking grooves 726, thus completing the installation of the receiving frame 700. As such, in the present invention, the receiving frame 700 can be securely mounted to the lower housing 100 in a one-touch assembly manner, thus making the process of assembling the air washer easy.

In the receiving frame 700, which is installed through the above-mentioned process, water in the lower housing 100 passes through the openings 715 and 725 in the receiving frame 700, so that the sterilizing chip sterilizes the water, thus preventing the propagation of bacteria in the water.

Figure 14:
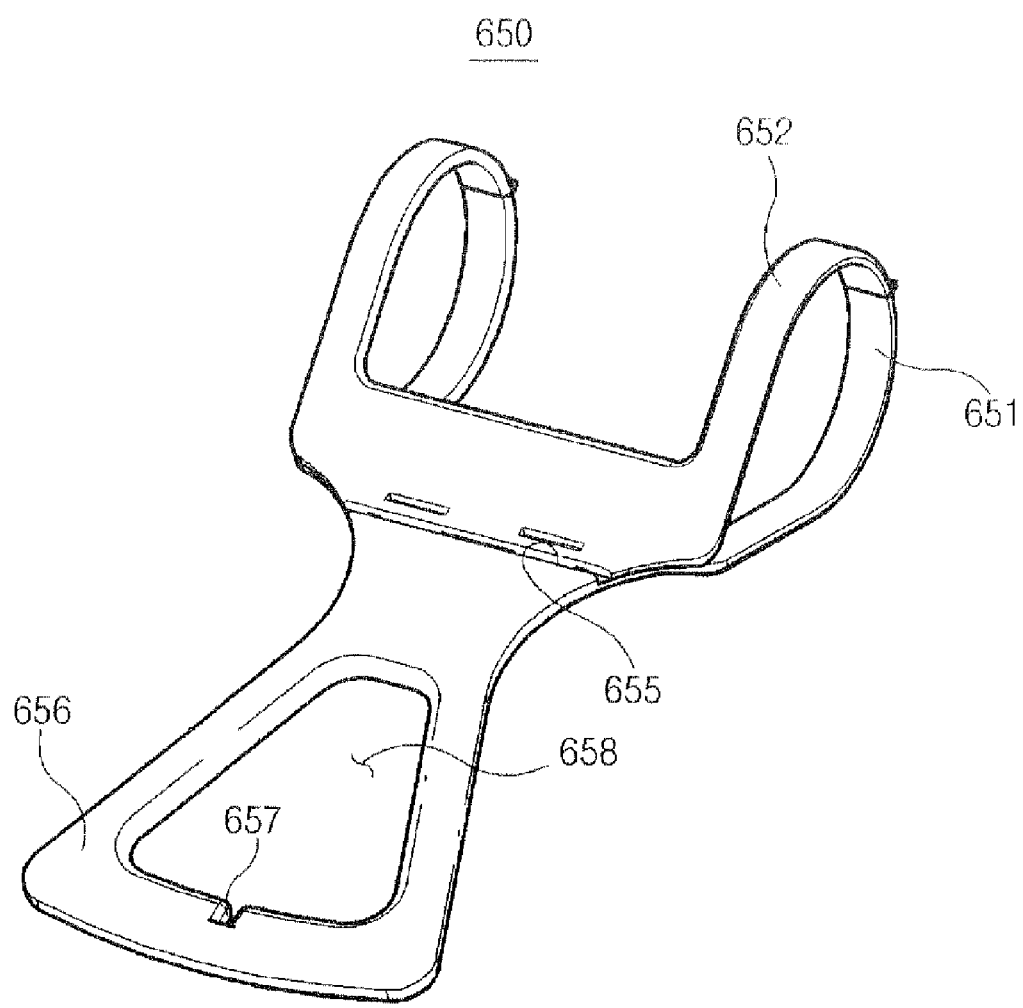
FIG. 14 is a perspective view of the disk shaft handle of FIG. 11.
Figure 15:
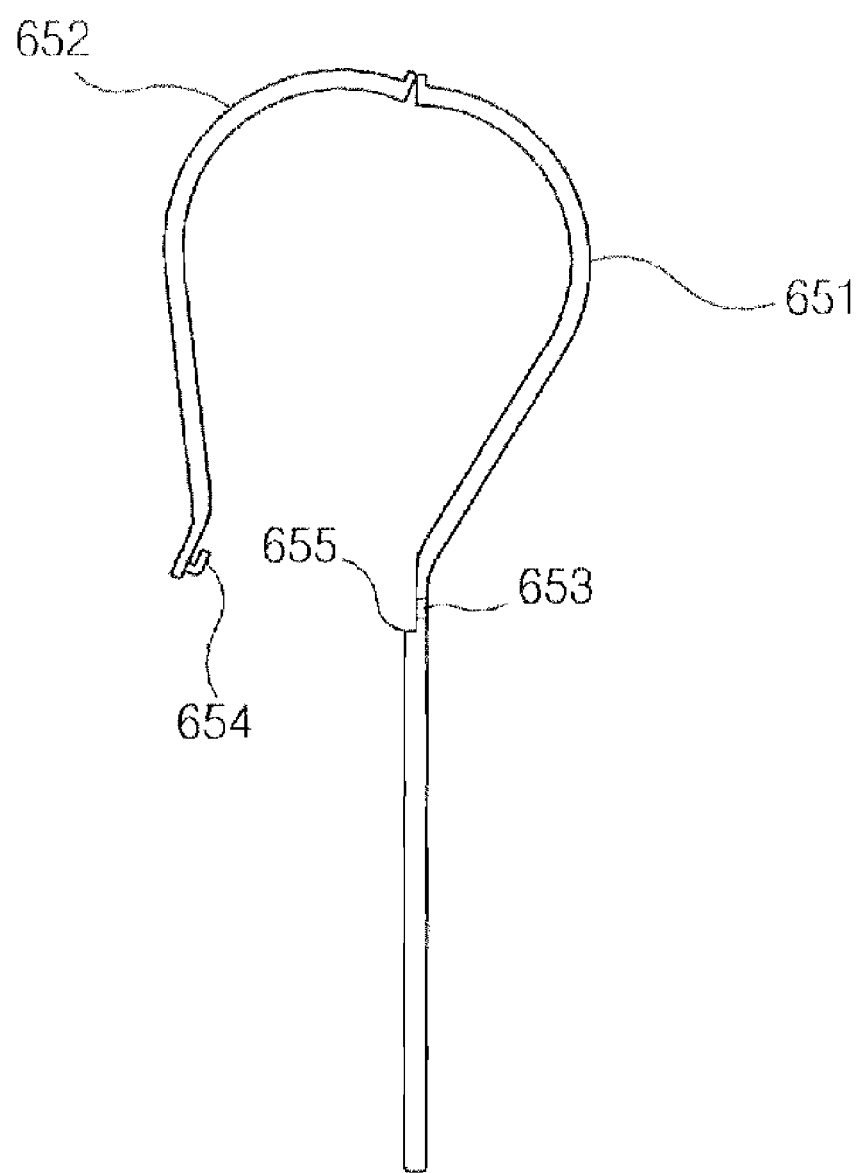
FIG. 15 is a side view of the disk shaft handle of FIG. 14.

Meanwhile, as shown in FIGS. 14 and 15, the disk shaft handle 650 is disposed in the lower housing 100, and includes an insert part 651, which is fitted over the disk shaft 610, and a grip part 656, which is connected to the insert part 651.

In detail, an insert opening 658 is formed through the grip part 656. An inset notch 657, which communicates with the insert opening 658, is formed in the grip part 656. The grip part 656 has a plate shape, which is reduced in width towards the insert part 651, thus generally forming a triangular shape. The insert opening 658 also has a shape such that the width thereof is reduced towards the insert part 651, so as to correspond to the entire shape of the grip part 656. The insert notch 657 is formed in the longitudinal direction of the disk shaft handle 650.

In a state in which the disk shaft handle 650 is fitted over the disk shaft 610, the grip part 656 thereof is seated into the handle seat 141 formed by the support rib 140 in the lower housing 100.

As such, the disk shaft handle 650 can be stably placed in the housing, so that it is prevented from being undesirably moved in a transverse direction, thus preventing noise attributable to friction.

Furthermore, when the disk shaft handle 650 is placed in the lower housing 100, the upper end of the support rib 140 of the lower housing 100 is inserted into the insert notch 657, so that the disk shaft handle 650 can be more effectively prevented from being moved in a transverse direction.

The insert part 651 includes a main body part, which is connected to the grip part 656, and a rotatable body part 652, which is rotatably connected to the main body.

Here, the rotatable body part 652 may be integrated with the main body part such that it is not rotatable with respect to the main body part.

The insert part 651 defines an insert hole, which is formed in the lateral direction of the disk shaft handle 650, and into which the disk shaft 610 is inserted. Here, the disk shaft 610 is rotatable with the insert part 651 in the state in which it is inserted into the insert part 651.

Furthermore, a cut mouth having a 'U' shape is formed in the insert part 651 in the longitudinal direction of the disk shaft handle 650, such that it communicates with the insert hole in the inset part 651.

In addition, a stop step 655, by which the rotatable body part 652 is stopped, is formed in the bottom of the main body part of the insert part 651 in the lateral direction of the disk shaft handle 650.

The stop step 655 serves to determine the position of the rotatable body part 652 when the rotatable body part 652 is fastened to the main body part, thus facilitating the process of inserting locking protrusions 654 of the rotatable body part 652 into respective locking holes 653 of the main body part.

As describe above, the locking slots 653 are formed in the main body part, and the locking protrusions 654 are provided on the rotatable body part 652.

In detail, the two locking slots 653, each of which extends a predetermined length, are formed through the main body part at opposite positions in the lateral direction of the disk shaft handle 650.

The locking protrusions 654 protrude from the inner surface of the free end of the rotatable body part 652.

Each locking protrusion 654 has a hook shape, so that it can be conveniently inserted into and locked to the corresponding locking slot 653, and the locking protrusion 654, which is locked thereto, can reliably maintain the locked state.

Furthermore, the junction between the rotatable body part 652 and the main body part is thinner than the other parts to function as a film hinge, so that the rotatable body part 652 is connected to the main body part so as to be rotatable around the film hinge, that is, the junction therebetween.

To assemble the disk shaft handle 650, having the above-mentioned construction, with the disk shaft 610, the main body part of the disk shaft handle 650 is placed on the spacer 630, which is fitted over the disk shaft 610. Thereafter, the rotatable body part 652 is rotated around the spacer 630, and the locking protrusions 654 are locked to the respective locking slots 653, thus completing the process of coupling the disk shaft handle 650 to the disk shaft 610. When it is desired to separate the disk shaft handle 650 from the disk shaft 610, the disk shaft handle 650 can be easily separated from the disk shaft 610 merely by releasing the locking protrusions 654 from the locking slots 653.

As such, the disk shaft handle 650 can be easily assembled with and disassembled from the disk shaft 610.

Furthermore, when the user inserts his/her fingers into the insert opening 658 and pulls the disk shaft handle 650 upwards, the disk assembly 600 is easily removed from the lower housing 100.

To assemble the air washer having the above-mentioned construction, the sterilizing unit is installed in the lower housing 100, and the disk assembly 600, provided with the disk shaft handle 650, is thereafter placed in the lower housing 100. Subsequently, the upper housing 200, having the drive unit, is coupled to the lower housing 100, thus completing the process of assembling the air washer.

In the air washer having the above-mentioned construction, air is drawn into the housing by the blower 900. Simultaneously, the disks 620 are rotated by the drive unit 500, so that parts of the disks 620 which have been wetted with water in the lower housing 100 are moved upwards. In this process, drawn air contacts the water applied to the parts of the disks 620 which are wetted with water. At this time, foreign substances in the air are transferred to the water and settle in the water in the lower housing 100. Furthermore, air is humidified and discharged outside through the air outlet ports 321.

Figure 25:
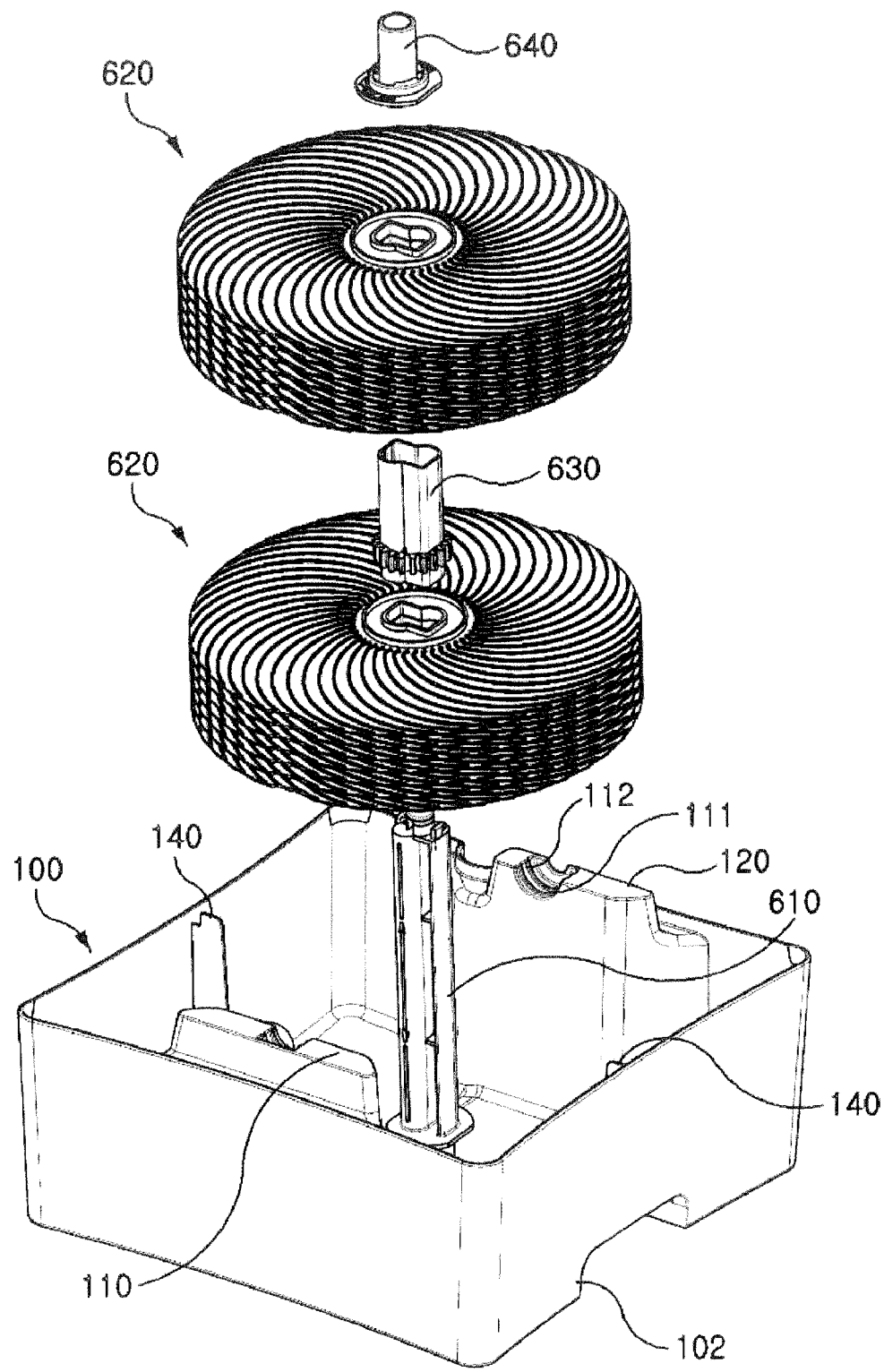
FIG. 25 is an exploded perspective view showing the structure for supporting a disk assembly of an air washer, according to another embodiment of the present invention.
Figure 26:
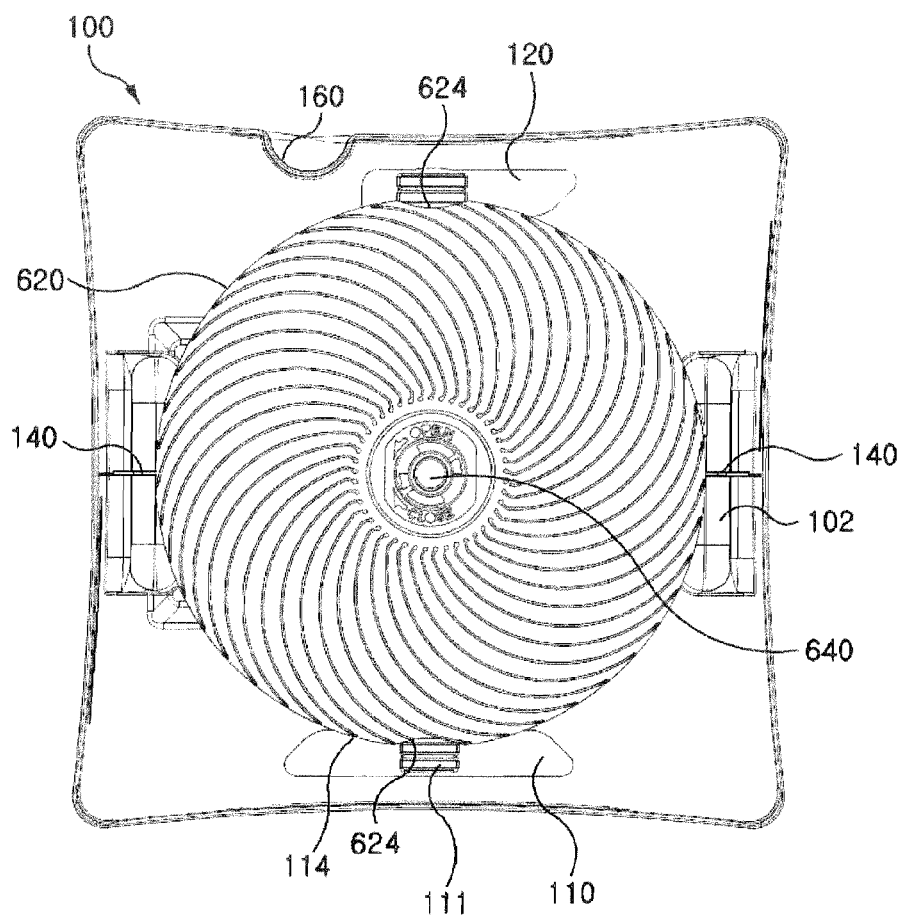
FIG. 26 is a plan view of FIG. 25.
Figure 27:
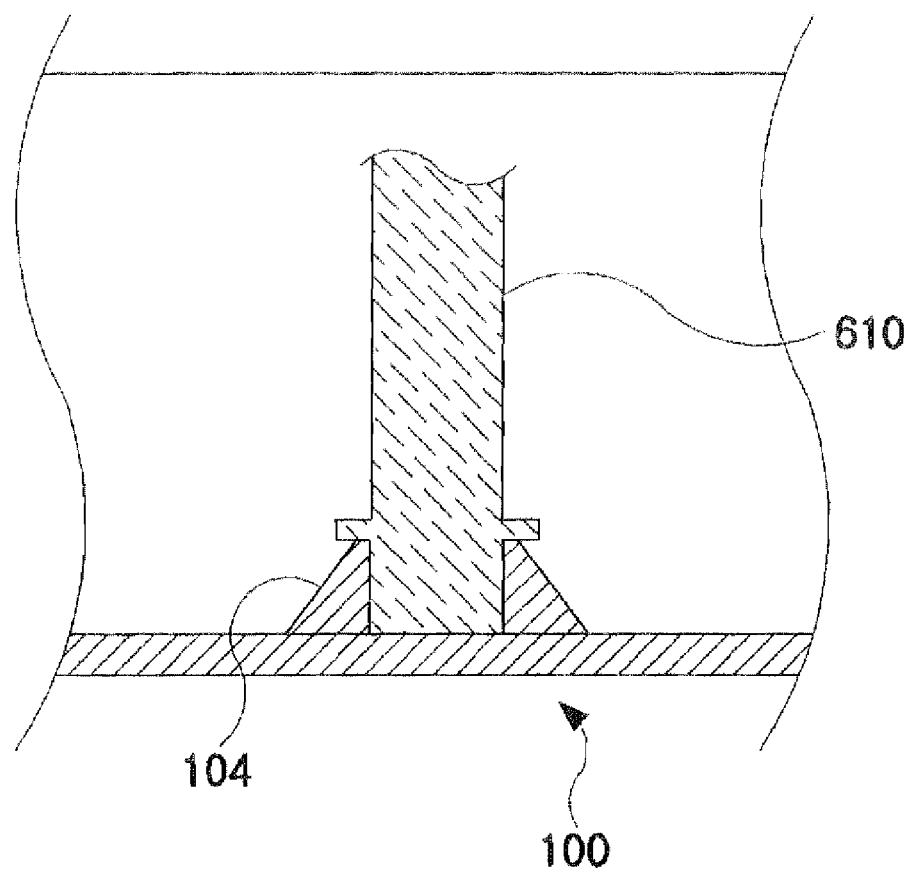
FIG. 27 is a partial sectional view showing the structure for supporting the disk assembly in a water reservoir of the air washer of FIG. 25.

FIGS. 25 through 27 illustrate an air washer having a humidifying function, according to another embodiment of the present invention.

FIG. 25 shows a water reservoir 100 to illustrate the internal structure thereof for temporarily supporting a disk assembly 600 when the disk assembly 600 is assembled or disassembled. FIG. 26 is a plan view of FIG. 25. FIG. 27 is a partial sectional view showing the structure of a support holding part for supporting a disk shaft of the disk assembly 600.

As shown in FIGS. 25 through 27, the support holding part 104 is provided at a central portion on the bottom of the water reservoir 100, so that, when the disk assembly 600 is assembled or disassembled, the disk shaft of the disk assembly 600 can be temporarily fastened to the support holding part 104.

Furthermore, a support means is provided on the inner surface of the water reservoir 100 to support the outer edges of the disks 620 of the disk assembly 600, which is fastened to the support holding part 104.

In this embodiment, a first support 110 and a second support 120, which are disposed at front and rear positions in the water reservoir 100 to support the disk shaft of the disk assembly 600, are used as the support means.

Furthermore, a seating depression 114, which forms an arc-shaped curved surface to support the outer edges of the disks 620, is formed in the inner surface of each of the first and second supports 110 and 120.

Moreover, handle parts 102, which are formed by compressing the left and right lower edges of the water reservoir 100 inwards and thus protrude from the bottom of the water reservoir 100, and support ribs 140, which protrude from the upper ends of the handle parts 102 to support the outer edges of the disks 620, may also be used as the support means.

In this embodiment, having the above-mentioned construction, when it is desired to assemble or disassemble the disk assembly 600, the disk shaft of the disk assembly 600 is fastened to the support holding part 104 on the bottom of the water reservoir 100, and the outer edges of the disks 620 are supported by the support means, which are provided at front, rear, left and right positions in the water reservoir 100. Thus, the disk assembly 600 can be stably supported without undesirably moving.

To assemble the air washer having the above-mentioned construction, the receiving frame 700 and the disk assembly 600 provided with the disk shaft handle 650 are installed in the water reservoir 100. Thereafter, the second upper housing 300, which holds the drive unit, and the first upper housing 400 are coupled to the water reservoir 100, thus completing the process of assembling the air washer.

In the air washer of the present invention, contaminated air is drawn into the air washer by the blower fan 910. Thereafter, while the drawn air passes through a filter, contaminants are removed from the air. Subsequently, the air passes through the disks 620, which are rotated in a state in which parts thereof are immersed in water. During this process, the air takes on moisture, and foreign substances, which were in the air, are removed from the air by the water. The air, which absorbs moisture, is discharged out of the air washer through the air outlet ports of the second upper housing 300.

Hereinafter, a method of controlling the air washer having the above-mentioned construction according to the present invention will be described.

The method of controlling the air washer of the present invention includes a detecting step of detecting whether the upper housing 200 and the lower housing 100 are separated from each other, and a controlling step of controlling the supply of power to the air washer according to whether the upper housing 200 and the lower housing 100 are separated from each other.

At the detecting step, the operation of detecting whether the upper housing 200 and the lower housing 100 are separated from each other may be conducted by various methods. For example, a sensor may be used, or, alternatively, the switch 800 may be used, as illustrated in the prior embodiment.

At the controlling step, a separate control unit, which is provided in the air washer, may control the power of the air washer using information obtained at the detecting step.

Alternatively, the air washer may be constructed such that the switch 800 conducts both the detecting operation and the power controlling operation, without having a separate control unit.

At the controlling step, the air washer is controlled such that, when the upper housing 200 is separated from the lower housing 100, the drive unit 500 of the air washer is turned off, and, when the upper housing 200 is coupled to the lower housing 100, the drive unit 500 of the air washer is turned on.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

As described above, an air washer having a humidifying function according to the present invention has the following advantages.

In the air washer of the present invention, a disk assembly includes a disk shaft, which has a stop ring on a first end thereof, disks, which are fitted over the disk shaft, and an end cap, which is coupled to the second end of the disk shaft. Therefore, when assembling the disk assembly, because the disks are fitted over the disk shaft in one direction and the end cap is coupled to the disk shaft in the same direction, there is an advantage in that the assembly process is simplified, so that the number of man-hours for the assembly process is reduced.

The disks are divided into a plurality of disk sets. A spacer is fitted over a disk shaft between the disk sets. Gear teeth are formed on the circumferential outer surface of the spacer. Thus, the spacer serves both to maintain the distance between the disk sets constant and to transmit rotating force from a motor to the disk shaft.

Furthermore, a flange is provided on the end cap, and a mounting protrusion is provided on the second end of the disk shaft. The mounting protrusion is bent in the circumferential direction of the disk shaft. An insert slot, into which the mounting protrusion is inserted, is formed in the flange. Thus, there is an advantage in that the process of assembling the end cap to the disk shaft is simple.

Each disk has a planar shape, and a plurality of ribs is provided on the surface of the disk in approximately radial directions. A stopper protrudes from the inner end of each rib.

Therefore, a relatively large amount of water can remain on the disk for a relatively long time.

Furthermore, a curved part, which is convex in the direction opposite the direction in which the disk is rotated, is formed in each rib. A bent part, which is bent to be convex in the direction opposite the direction in which the disk is rotated, is formed in each rib between the curved part and the stopper. Thus, when the disks are rotated, a relatively large amount of water can be drawn up by the curved parts. As well, thanks to the bent parts, water is prevented from being removed from the disks even when the disks are rotated.

The air washer of the present invention further includes a switch. The switch includes a switch body, and a switching bar, which is provided on the switch body to turn on or off the power of the air washer. A support member for supporting the switching bar is provided in the lower housing, so that, when the upper housing is separated from the lower housing, the supply of power to the air washer is automatically interrupted. Therefore, when a user separates the upper housing from the lower housing to supplement water or clean the disks, the user can be prevented from being injured by a blower fan or other components, and the air washer is prevented from being damaged.

The air washer further includes a bracket, which is provided in the upper housing and has therein a switch seat, into which the switch is seated. Two first mounting hooks are provided at opposite positions in the bracket, and two second mounting hooks are provided in the upper housing at positions corresponding to the respective first mounting hooks. Thus, the switch can be easily installed in the housing through a simple installation structure.

Furthermore, the bracket further includes locking hooks, which are provided in the bracket at opposite sides of the switch seat. Thus, the switch can be securely mounted to the bracket using the locking hooks.

In addition, a handle seat, into which a grip part of a disk shaft handle is seated, is formed in the housing, so that the disk shaft handle can be stably placed in the housing. Thus, the disk shaft handle is prevented from being undesirably moved to the left or right, thereby reducing noise attributable to friction.

As well, a surface of the part of the housing, which has the handle seat defined therein, is inclined at a predetermined angle, so that the disk shaft handle, which is placed in the housing in a state in which it is fitted over the disk shaft, can maintain its position more stably.

A support rib is vertically provided on the inner surface of the housing, and the handle seat is formed in the upper edge of the support rib. Therefore, the space for forming the handle seat is relatively small, so that the space inside the housing is increased.

In addition, the disk shaft has a cross-section such that the upper and lower portions thereof are asymmetrical to each other, based on the horizontal line passing through the center thereof, and such that the left and right portions thereof are asymmetrical to each other based on the vertical line, passing through the center thereof. Therefore, the disks are prevented from being fitted over the disk shaft in the wrong direction.

Moreover, the disk shaft is shaped such that a cross-section thereof has a symmetrical structure with respect to the diagonal direction based on the center thereof. Thus, when the disks are placed on the support surface in a state in which they are fitted over the disk shaft, the disks remain balanced and thus maintain the stationary state.

Furthermore, the opposite ends of the disk shaft, over which the disks are fitted, are differently shaped from each other, so that the disks are prevented from being rotated in the wrong direction, thus power can be reliably transmitted from the drive unit to the disk shaft. Particularly, in the case where the arc-shaped ribs are formed on the surface of the disks, the disk shaft can be installed in the correct direction, in which the ribs can correctly draw up water, thus improving the contaminant settling efficiency and air humidifying efficiency of the air washer.

Meanwhile, shaft seats are formed in the supports for supporting the disk shaft. The disk shaft has a support protrusion on the second end thereof, such that the second end of the disk shaft, having the support protrusion, is longer than the first end thereof. Furthermore, a stop piece is provided in one of the shaft seats, which are shaped differently from each other. Therefore, even if an attempt is made to seat the second end of the disk shaft into the shaft seat having the stop piece, because the support protrusion interferes with the stop piece, incorrect assembly can be fundamentally prevented.

In the present invention, air inlet ports have inlet air guide blades. Thus, efficiency with which air flows towards the center of the blower fan can be increased, thus enhancing the contaminant settling efficiency and air humidifying efficiency of the air washer.

Furthermore, when seen in a plan view, each of the four sidewalls of the housing has a concave arc shape. The air inlet ports are formed in three regions in the upper surface of the housing, that is, in the rear portion and opposite side portions of the upper surface of the housing. In addition, the inlet air guide blades are inclined downwards towards the center of the blower fan and are arranged in an arc-shaped arrangement along the sidewalls of the housing. Therefore, the external appearance of the air washer is superior, and the efficiency with which air is drawn towards the center of the blower fan is improved, thus further enhancing the contaminant settling efficiency and air humidifying efficiency of the air washer.

In the present invention, a sterilizing unit is provided in the water reservoir. Therefore, the present invention does not require a process of mixing liquid sterilizing agent with water in the water reservoir, thus being convenient for the user.

Furthermore, the sterilizing unit is disposed ahead of front sides of the disks, which are parts of the disks that enter water when the disks are rotated. As such, because the sterilizing unit is disposed at a position at which water currents are generated, sterilizing substances can be smoothly drawn out of the sterilizing unit, and the sterilizing substances can be evenly dispersed in water in the water reservoir.

In addition, in the case where the disks are divided into a first disk set and a second disk set, the sterilizing unit is disposed between the first and second disk sets, ahead of front sides of the disks, thus further enhancing the efficiency with which the sterilizing substances are eluted from the sterilizing unit and are dispersed in water in the water reservoir.

Meanwhile, installation protrusions for supporting the receiving frame of the sterilizing unit are provided in the housing. A cut slot is formed in each installation protrusion in the direction in which the receiving frame is fitted into the installation protrusions. Thus, when the receiving frame is fitted into or removed from the installation protrusions, the installation protrusions can be elastically moved, so that the process of assembling or removing the receiving frame can be smoothly conducted.

Meanwhile, to determine the optimum distance between disks in the disk assembly, the present invention uses a method in which, after several models, which have various flow rates and flow rate uniformities depending on the distances between disks, are sampled, the model that has the largest number of disks despite having a relatively low flow rate uniformity is determined to be the optimum model. Thus, the humidifying efficiency, accomplished by the rotation of the disks, can be enhanced.

Alternatively, in the method of determining the optimum distance between disks in the disk assembly, a method in which several models, which have various flow rates and flow rate uniformities depending on the distances between disks, are sampled, and, thereafter, among the sampled models, a model, the flow rate uniformity of which is 0.35 or less, is determined to be the optimum model, may be used. Thus, the humidifying efficiency attributable to the rotation of the disks can be further enhanced.

Moreover, the present invention may be constructed such that the distance between the disks of the disk assembly ranges from 6.5 mm to 6.8 mm to maximize the humidifying efficiency accomplished by the rotation of the disks.

Meanwhile, in the present invention, a support holding part may be provided on the bottom of the water reservoir, such that the disk shaft of the disk assembly can be temporarily fastened to the support holding part. In this case, when it is desired to clean the disks, the disk assembly is removed from the housing, and, thereafter, the disk shaft of the disk assembly is temporarily fastened to the support holding part. Subsequently, the disk assembly is disassembled, and the operation of cleaning the disks is conducted. Therefore, the cleaning operation can be conveniently conducted. Furthermore, compared to the conventional art, in which the disk assembly is separated from the water reservoir and is moved outside the water reservoir to conduct the cleaning operation, the present invention can solve a problem in which water falls onto the support surface when the disk assembly is moved outside the water reservoir. In addition, the present invention prevents the disks from being damaged, which may occur when they are moved. As well, the present invention can solve a problem in that, when the disk assembly is disassembled and various elements of the disk assembly are thus placed on the support surface, a relatively large amount of space is required.

Furthermore, a support means, which can support the disks when the disk shaft is fastened to the support holding part, is provided in the water reservoir. Therefore, when the disk assembly is fastened to the support holding part to conduct the operation of cleaning the disks, the outer edges of the disks can be stably supported by the support means. Thus, during the process of assembling or disassembling the disk assembly, the disk assembly is reliably prevented from being undesirably moved forwards, backwards, leftwards or rightwards.

Here, the supports for supporting the disk shaft or handle parts, which are formed by protruding the bottom of the water reservoir inwards, are used as the support means. Therefore, the structure of the support means for supporting the disks is simple.

Furthermore, in the case where the handle parts and support frames, which are provided on the handle parts to support the disks, are used as the support means, there is an advantage in that the utilization of space in the water reservoir can be increased.

Meanwhile, a rolling prevention means may be formed on the circumferential outer edge of each disk. In this case, even if the disk assembly is placed on the support surface, for example, to conduct the operation of cleaning the disks, the disk assembly is prevented from undesirably rolling on the support surface.

In the case where the rolling prevention means is realized by cutting parts of the outer edges of the disks, there are advantages in that the process of manufacturing the disk is simple and the weight of the disk is reduced.

Furthermore, in the present invention, an outer rim is provided on the surface of each disk at a position spaced apart from the fitting hole of the disk. Thus, the distance between adjacent disks can be maintained constant using the outer rim. In addition, the outer rim serves to prevent water from entering the fitting hole of the disk, so that, even when the disks are used for a long period, foreign substances are prevented from being held in the fitting hole.

Moreover, an inner rim is provided between the fitting hole and the outer rim. Therefore, the inner rim and the outer rim form a double water permeation structure, such that water is prevented from entering the fitting hole of the disk.

Meanwhile, in the present invention, a shroud, which surrounds the blower fan, is provided in the housing such that it protrudes from the housing, thus reducing noise attributable to the operation of the blower fan, and increasing the flow rate of air drawn into the housing by the blower fan.

Furthermore, an air inflow passage, which is defined in the first upper housing, has a rectangular cross-section, and an air inflow passage, which is defined by the shroud, has a circular cross-section. Therefore, when air is drawn into the housing by the blower fan, air currents are rapidly varied, and the generation of an air vortex is promoted, thus reducing noise and increasing the flow rate of air.

What is claimed is:

1. An air washer having a humidifying function, comprising:
   a housing having an air inlet port and an air outlet port therein;
   a blower fan for drawing air into the housing and discharging the air outside the housing;
   a disk assembly removing foreign substances from the air and humidifying the air; and
   a drive unit operating the blower fan and the disk assembly,
   wherein the disk assembly comprises a disk shaft, and a plurality of disks fitted over the disk shaft, the disks having a planar shape, and a plurality of ribs are arranged between a center of the disks and an outer edge thereof on at least one surface of the disks in a radial direction by protrusion,
   wherein the disk assembly further comprises a disk shaft handle, comprising an insert part to be fitted over the disk shaft, and a grip part connected to the insert part,
   wherein the housing comprises a water reservoir, the air washer further comprising:
   a sterilizing unit installed in the water reservoir, and
   the sterilizing unit comprises a sterilizing chip, and a receiving frame for removably receiving the sterilizing chip therein, and
   an installation slot, into which the receiving frame is inserted, is formed in the water reservoir, wherein the installation slot is formed in an installation protrusion provided on the inner surface of the water reservoir.

2. The air washer as set forth in claim 1, wherein the disk shaft has a stop ring on a first end thereof, and the disk assembly further comprises an end cap fitted over a second end of the disk shaft.

3. The air washer as set forth in claim 2, wherein the disk assembly further comprises a spacer fitted over the disk shaft between the disks, with gear teeth formed on a circumferential outer surface of the spacer.

4. The air washer as set forth in claim 2, wherein
   a flange is provided on the end cap,
   a mounting protrusion protrudes from the second end of the disk shaft, the mounting protrusion being bent in a circumferential direction of the disk shaft, and an insert slot is formed through the flange, so that the mounting protrusion is inserted into the insert slot.

5. The air washer as set forth in claim 1, wherein a stopper protrudes from an end of the rib in a circumferential direction.

6. The air washer as set forth in claim 5, wherein
a curved part is formed in the rib, the curved part being convex in a direction opposite a direction in which the disk is rotated, and
a bent part is formed in the rib between the curved part and the stopper, the bent part being bent convex in a direction opposite the direction in which the disk is rotated.

7. The air washer as set forth in claim 1, wherein
the housing comprises an upper housing, and a lower housing provided under the upper housing,
the air washer further comprising:
a switch provided in the upper housing, and comprising a switch body, and a switching bar provided on the switch body to turn on or off power of the air washer, wherein
a support member for supporting the switching bar is provided in the lower housing.

8. The air washer as set forth in claim 7, further comprising:
a bracket provided in the upper housing, the bracket having therein a switch seat, into which the switch is seated, wherein
first mounting hooks are provided at opposite positions in the bracket, and
second mounting hooks are provided in the upper housing at positions corresponding to the respective first mounting hooks such that the second mounting hooks face the respective first mounting hooks.

9. The air washer as set forth in claim 7, further comprising:
a bracket provided in the upper housing, the bracket having therein a switch seat, into which the switch is seated, wherein
locking hooks are provided in the bracket at respective opposite sides of the switch seat.

10. The air washer as set forth in claim 1, further comprising:
a handle seat for seating the grip part of the disk shaft handle thereinto is formed in the housing.

11. The air washer as set forth in claim 10, wherein a surface of a part of the housing onto which the grip part of the disk shaft handle is seated is inclined at a predetermined angle.

12. The air washer as set forth in claim 10, wherein a support rib is provided on an inner surface of a sidewall of the housing, and the handle seat is formed in an upper edge of the support rib.

13. The air washer as set forth in claim 1, wherein the disk shaft has a cross-section such that upper and lower portions thereof are asymmetrical based on a horizontal line passing through a center thereof, and such that left and right portions thereof are asymmetrical based on a vertical line passing through the center thereof.

14. The air washer as set forth in claim 13, wherein the cross-section of the disk shaft is symmetric with respect to a diagonal direction based on the center thereof.

15. The air washer as set forth in claim 13, wherein the cross-section of the disk shaft has at an upper end thereof a first convex part, which is convex upwards, and has at a lower end thereof a second convex part, which is convex downwards such that the first and second convex parts are oriented in opposite directions.

16. The air washer as set forth in claim 1, wherein the housing comprises a water reservoir, and shaft seats, into which respective opposite ends of the disk shaft are seated, are formed in the water reservoir, the shaft seats being shaped differently from each other.

17. The air washer as set forth in claim 16, wherein a diameter of a first end of the disk shaft is less than a diameter of a second end thereof, so that the first and second ends of the disk shaft are differently shaped from each other.

18. The air washer as set forth in claim 16, wherein a length of a first end of the disk shaft is less than a length of a second end thereof, so that the first and second ends of the disk shaft are differently shaped from each other.

19. The air washer as set forth in claim 18, wherein a stop piece is provided in a first shaft seat of the differently shaped shaft seats, so that, when the second end of the disk shaft, which is longer than the first end thereof, is seated in the first shaft seat, the stop piece interferes with the second end of the disk shaft to prevent the second end of the disk shaft from being seated in the first shaft seat.

20. The air washer as set forth in claim 16, wherein a plurality of ribs, each having an arc shape, is provided on a surface of each of the disks.

21. The air washer as set forth in claim 1, wherein the air inlet port comprises a plurality of air inlet ports, and a plurality of inlet air guide blades is provided in each of the air inlet ports such that air drawn into the air inlet port is guided towards a center of the blower fan.

22. The air washer as set forth in claim 21, wherein each of the inlet air guide blades is inclined downwards and towards the center of the blower fan and is formed in an arc shape along a corresponding sidewall of the housing.

23. The air washer as set forth in claim 21, wherein each of four sidewalls of the housing has a concave arc shape when seen in a plan view, and the air inlet ports are formed in an upper surface of the housing at three respective portions including a portion adjacent to a rear wall of the housing and portions adjacent to opposite sidewalls of the housing, each of the air inlet ports having a triangular shape.

24. The air washer as set forth in claim 1, wherein the sterilizing unit is disposed ahead of front sides of the disks, at which the disks enter water in the water reservoir when the disk is rotated.

25. The air washer as set forth in claim 24, wherein the disk assembly comprises a first disk set and a second disk set, and the sterilizing unit is disposed ahead of the front sides of the disks between the first and second disk sets.

26. The air washer as set forth in claim 1, wherein
a locking groove is formed in an outer surface of the receiving frame, so that, when the receiving frame is inserted into the installation slot of the installation protrusion, a locking protrusion provided on the installation protrusion is inserted into the locking groove.

27. The air washer as set forth in claim 26, wherein a cut slot is formed in the installation protrusion in a direction in which the receiving frame is inserted into the installation slot of the installation protrusion.

28. The air washer as set forth in claim 1, wherein a fitting hole is formed through the disk, the disk shaft is fitted into the fitting hole, and an outer rim is provided on the disk around the fitting hole at a position spaced apart from the fitting hole.

29. The air washer as set forth in claim 28, wherein an inner rim is provided on the disk between the fitting hole and the outer rim.

30. The air washer as set forth in claim 1, wherein rolling prevention means is formed in an outer edge of the disk.

31. The air washer as set forth in claim 30, wherein the rolling prevention means is formed by depressing part of the outer edge of the disk.

32. The air washer as set forth in claim 1, wherein the disk assembly comprises a plurality of disks, and a distance between adjacent disks ranges from 6.5 mm to 8.6 mm.

33. The air washer as set forth in claim 1, further comprising:

a shroud surrounding the blower fan, the shroud protruding a surface of the housing outwards.

34. The air washer as set forth in claim 33, wherein the housing comprises:

a first upper housing; and a second upper housing coupled to a lower end of the first upper housing, wherein the air inlet port for drawing air is formed in an upper surface of the first upper housing, and the outlet port for discharging air is formed in a sidewall of the second upper housing.

35. The air washer as set forth in claim 34, wherein an air inflow passage, which is defined in the first upper housing, has a rectangular cross-section, and an air inflow passage, which is defined by the shroud, has a circular cross-section.

* * * * *